US011103274B2

(12) United States Patent
Isakov et al.

(10) Patent No.: US 11,103,274 B2
(45) Date of Patent: Aug. 31, 2021

(54) SYSTEM AND METHOD FOR LAPAROSCOPIC MORCELLATOR

(71) Applicants: BRIGHAM AND WOMEN'S HOSPITAL, INC., Boston, MA (US); PRESIDENT AND FELLOWS OF HARVARD COLLEGE, Cambridge, MA (US)

(72) Inventors: Alexander Isakov, Sudbury, MA (US); Kimberly Murdaugh, Cambridge, MA (US); William Burke, Sudbury, MA (US); Jon Einarsson, Boston, MA (US); Conor Walsh, Cambridge, MA (US)

(73) Assignees: THE BRIGHAM AND WOMEN'S HOSPITAL, Boston, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 76 days.

(21) Appl. No.: 16/376,549

(22) Filed: Apr. 5, 2019

(65) Prior Publication Data

US 2019/0365407 A1 Dec. 5, 2019

Related U.S. Application Data

(63) Continuation of application No. 14/775,053, filed as application No. PCT/US2014/020649 on Mar. 5, 2014, now Pat. No. 10,258,364.

(Continued)

(51) Int. Cl.
*A61B 17/3205* (2006.01)
*A61B 17/32* (2006.01)
(Continued)

(52) U.S. Cl.
CPC ...... *A61B 17/32056* (2013.01); *A61B 17/221* (2013.01); *A61B 17/320016* (2013.01);
(Continued)

(58) Field of Classification Search
CPC ... A61B 17/00; A61B 17/00234; A61B 17/22; A61B 17/221; A61B 17/28;
(Continued)

(56) References Cited

U.S. PATENT DOCUMENTS

| 4,368,734 A | 1/1983 | Banko |
| 5,336,237 A | 8/1994 | Chin et al. |

(Continued)

FOREIGN PATENT DOCUMENTS

| WO | 9709922 A1 | 3/1997 |
| WO | 2014158880 A1 | 10/2014 |

(Continued)

OTHER PUBLICATIONS

ISA/EPO. International Search Report for PCT/US2016/061595 (Lattis Surgical Inc.) dated Jan. 24, 2017, 4 pages.
(Continued)

*Primary Examiner* — Sarah W Aleman
(74) *Attorney, Agent, or Firm* — Winthrop & Weinstine, P.A.

(57) ABSTRACT

Embodiments of the invention provide a laparoscopic morcellating device and method for removing tissue from a body cavity. The morcellating device includes a containment mechanism having an aperture, a cutting mechanism designed to fit into an interior space of the containment mechanism and a retractor mechanism that is coupled to the cutting mechanism. The containment mechanism and cutting mechanism combination surrounds the tissue and the aperture of the containment mechanism is closed around the tissue. The morcellating device further includes a motor for
(Continued)

actuating the retractor such that the cutting mechanism constricts and morcellates the tissue. The laparoscopic morcellating device further allows for torque balancing of the retractor mechanism, gas flow regulation of the body cavity, and safety feedback mechanisms that can alert the surgeon.

15 Claims, 11 Drawing Sheets

Related U.S. Application Data

(60) Provisional application No. 61/783,000, filed on Mar. 14, 2013.

(51) Int. Cl.
*A61B 17/221* (2006.01)
*A61B 17/00* (2006.01)
*A61B 17/34* (2006.01)
*A61B 90/00* (2016.01)

(52) U.S. Cl.
CPC ..... *A61B 17/32002* (2013.01); *A61B 17/3421* (2013.01); *A61B 2017/0003* (2013.01); *A61B 2017/00075* (2013.01); *A61B 2017/00123* (2013.01); *A61B 2017/00287* (2013.01); *A61B 2017/00398* (2013.01); *A61B 2017/00876* (2013.01); *A61B 2017/2212* (2013.01); *A61B 2017/320024* (2013.01); *A61B 2090/0811* (2016.02)

(58) Field of Classification Search
CPC ............... A61B 17/2909; A61B 17/32; A61B 17/32002; A61B 17/32056; A61B 17/320725; A61B 2017/00367; A61B 2090/064; A61B 2090/065; A61B 2090/0811; A61M 25/0133; A61F 2/95; A61F 2/01
See application file for complete search history.

(56) References Cited

U.S. PATENT DOCUMENTS

| | | | |
|---|---|---|---|
| 5,354,303 | A | 10/1994 | Spaeth et al. |
| 5,569,284 | A | 10/1996 | Young et al. |
| 5,611,803 | A | 3/1997 | Heaven et al. |
| 5,735,289 | A | 4/1998 | Pfeffer et al. |
| 5,836,953 | A | 11/1998 | Yoon |
| 6,451,036 | B1* | 9/2002 | Heitzmann .... A61B 17/320758 606/159 |
| 6,537,273 | B1 | 3/2003 | Sosiak et al. |
| 9,522,034 | B2 | 12/2016 | Johnson et al. |
| 9,629,618 | B2 | 4/2017 | Davis et al. |
| 2004/0002683 | A1 | 1/2004 | Nicholson et al. |
| 2005/0267492 | A1 | 12/2005 | Poncet et al. |
| 2008/0221604 | A1* | 9/2008 | Kondoh .......... A61B 17/32056 606/170 |
| 2009/0326546 | A1* | 12/2009 | Mohamed ........ A61B 17/00234 606/114 |
| 2011/0040314 | A1 | 2/2011 | McGuckin, Jr. et al. |
| 2011/0046637 | A1 | 2/2011 | Patel |
| 2012/0203241 | A1 | 8/2012 | Williamson |
| 2016/0030073 | A1 | 2/2016 | Isakov et al. |
| 2016/0100857 | A1 | 4/2016 | Wachli et al. |

FOREIGN PATENT DOCUMENTS

| | | | |
|---|---|---|---|
| WO | 2015164591 | A1 | 10/2015 |
| WO | 2017083694 | A1 | 5/2017 |
| WO | 2018119473 | A1 | 6/2018 |

OTHER PUBLICATIONS

ISA/RU, International Search Report and Opinion for PCT/US 2017/068365 ( Brigham and Women's Hospital, Inc. et al.) dated Apr. 19, 2018, 9 pages.
ISA/EPO International Search Report for PCT/US2016/061595 (Latts Surgical Inc.) dated Jan. 24, 2017, 4 pages.
ISA-RU, International Search Report and Opinion for PCT/US2017/ 068365 (Brigham and Women's Hospital, Inc. et al., dated Apr. 19, 2019, 9 pages.
International Search Report and Written Opinion dated Jun. 23, 2014, in connection with PCT/US2014/020649.

* cited by examiner

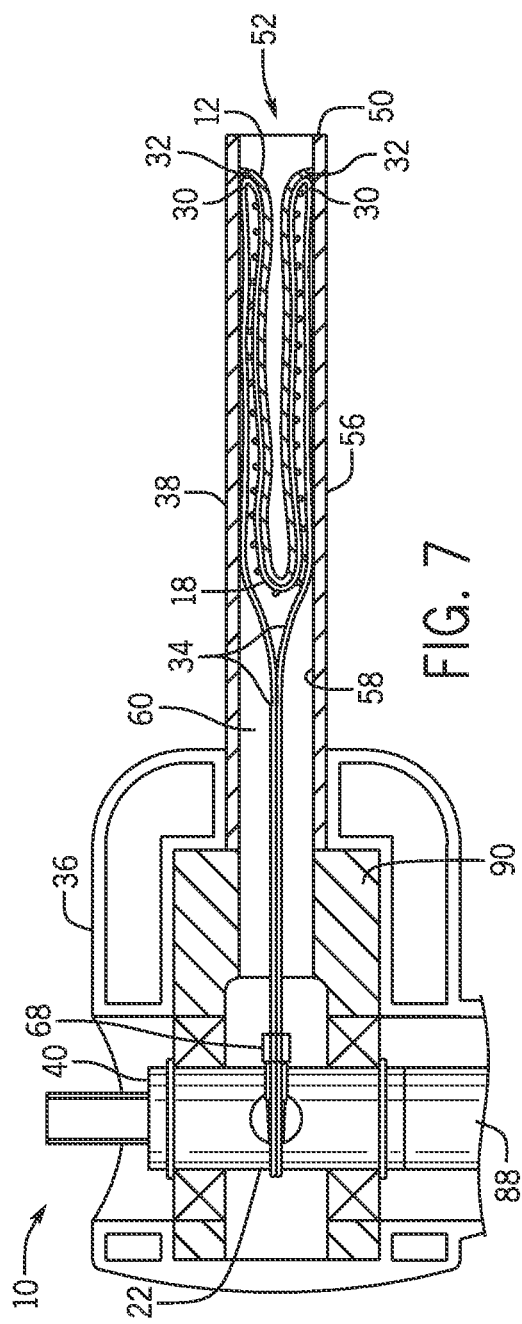
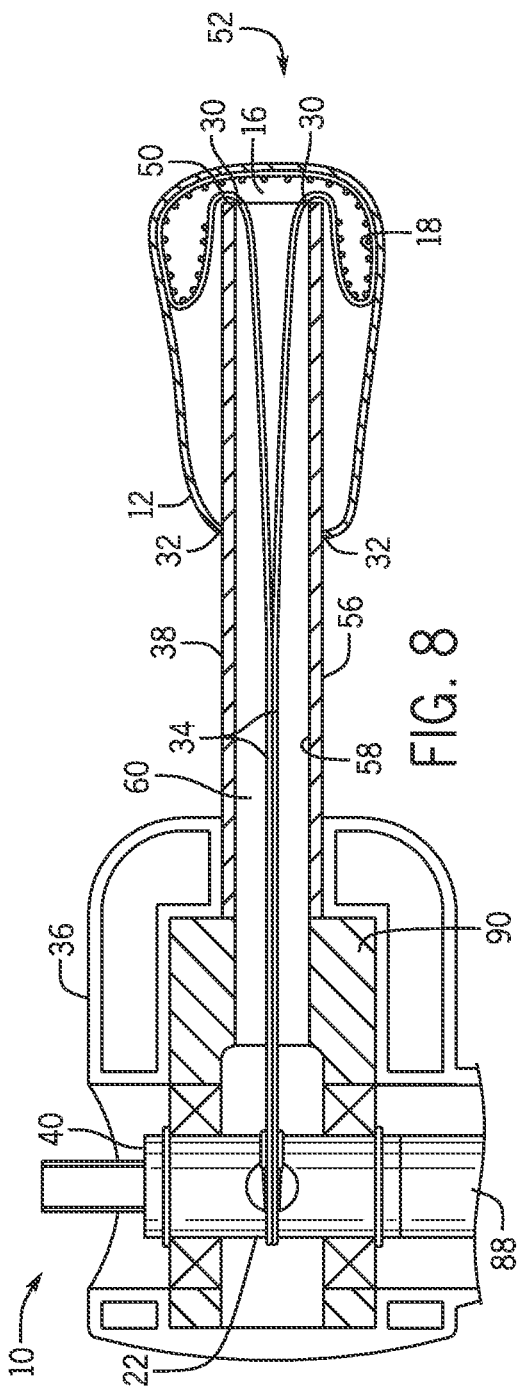

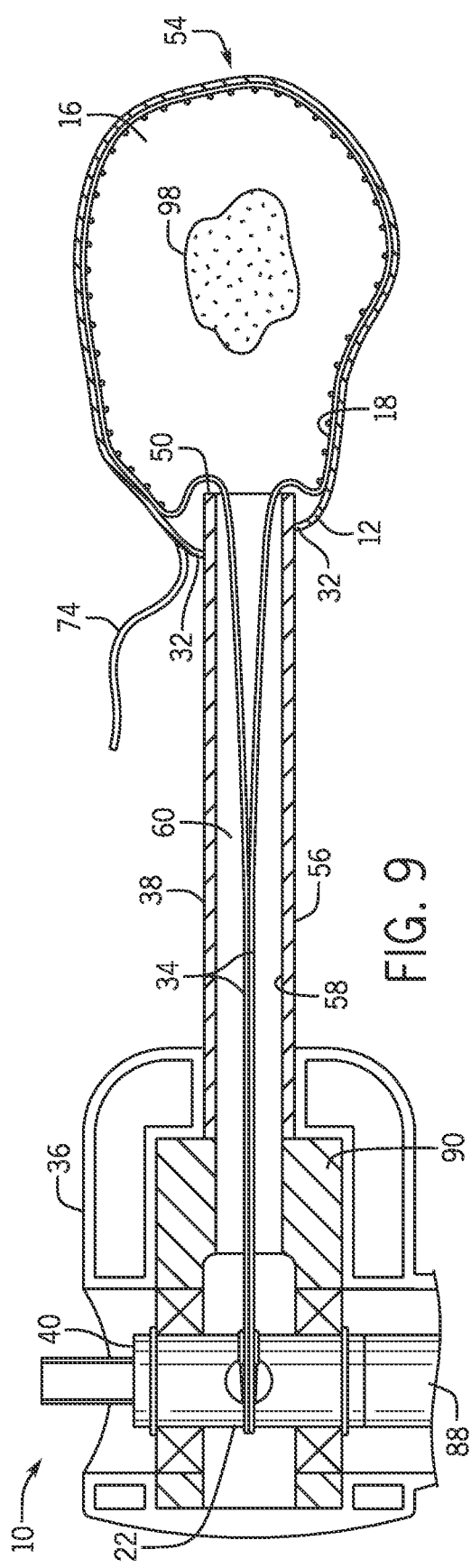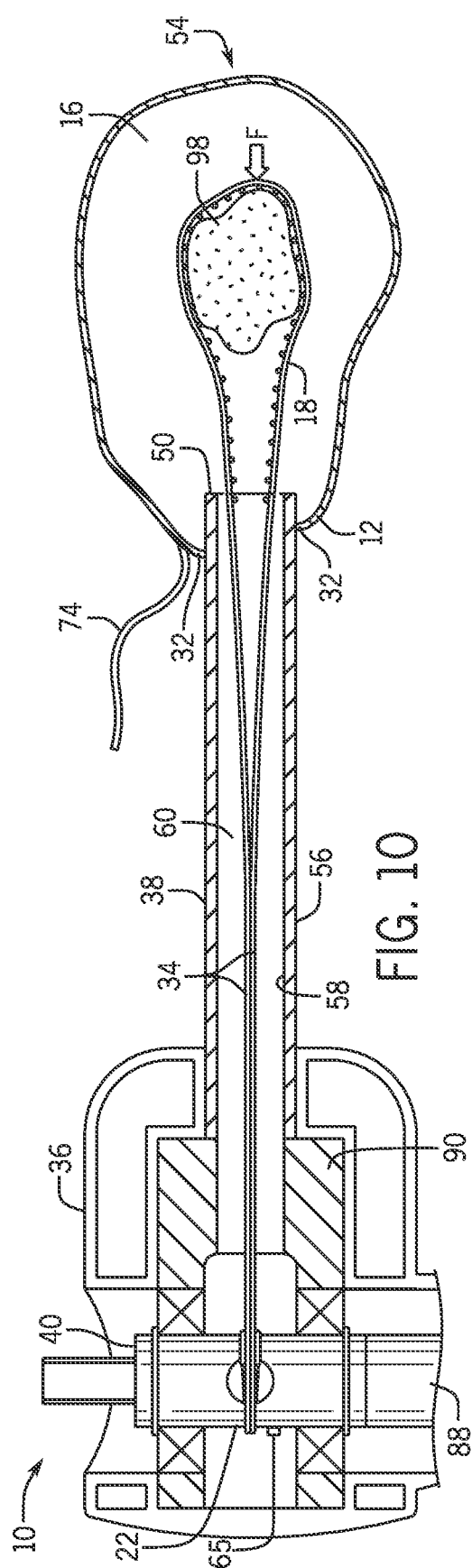

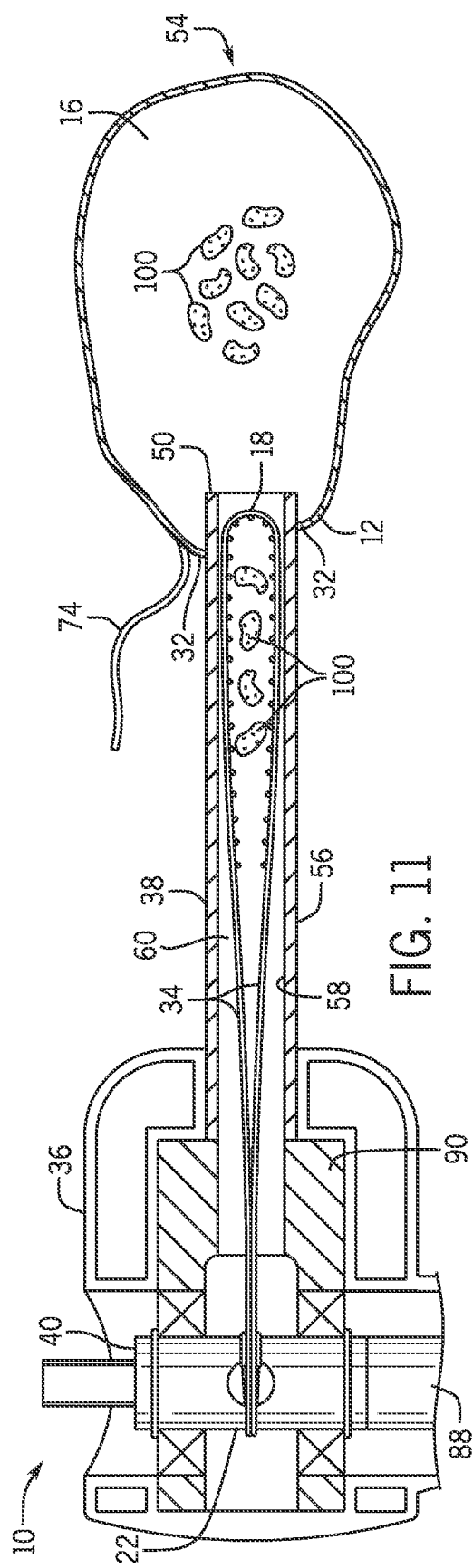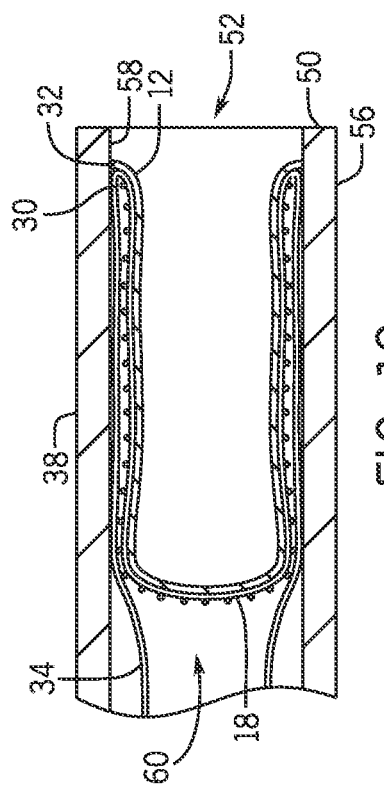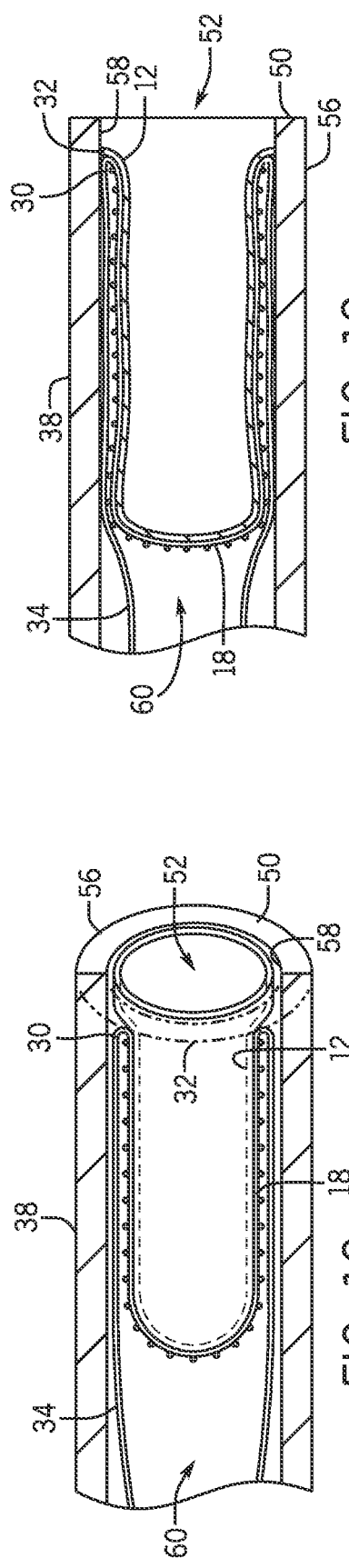

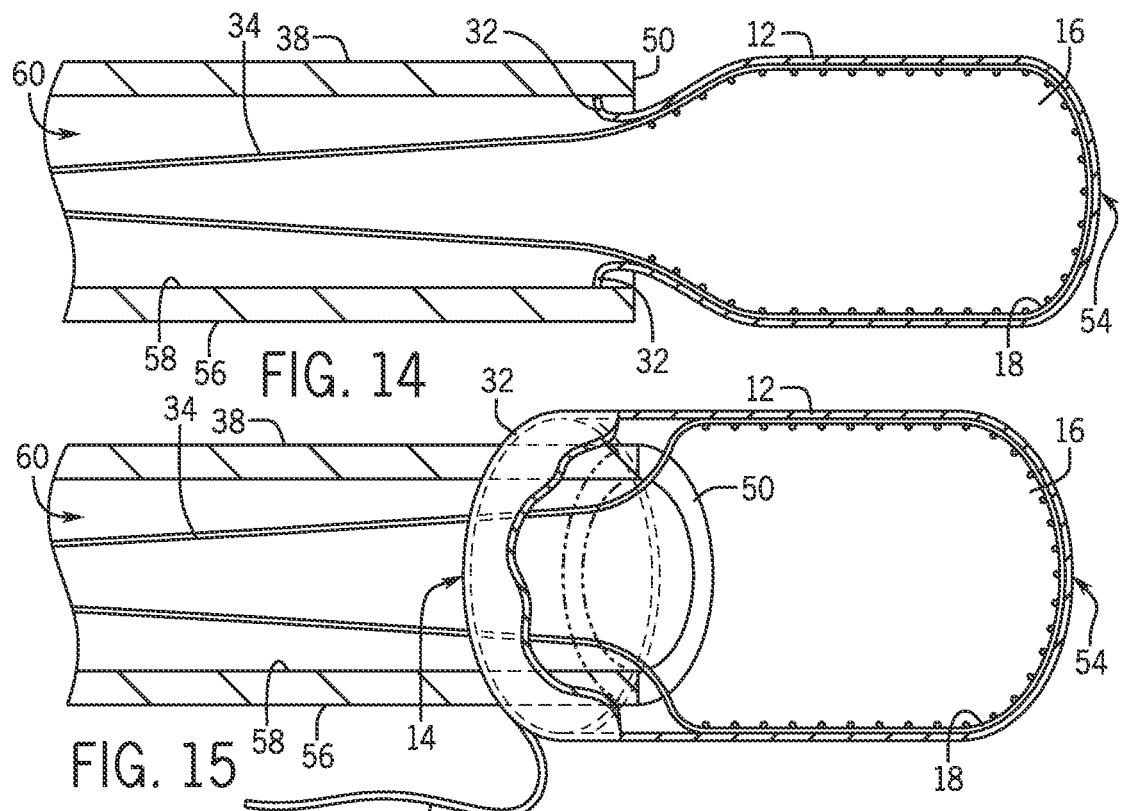
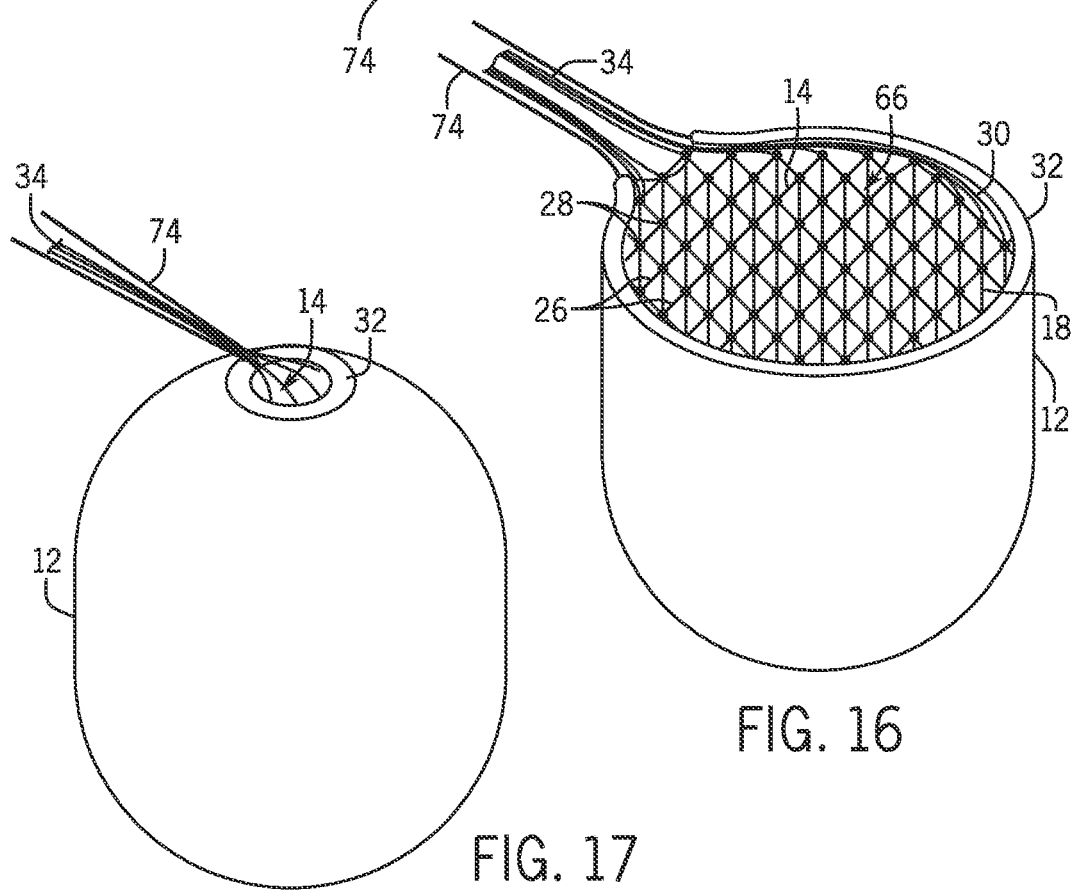

SYSTEM AND METHOD FOR LAPAROSCOPIC MORCELLATOR

CROSS REFERENCE TO RELATED APPLICATIONS

The present application is a continuation of U.S. patent application Ser. No. 14/775,053, filed Sep. 11, 2015 (U.S. Pat. No. 10,258,364), which is a 371 application of PCT/US2014/020649 filed Mar. 5, 2014, which claims priority to, and incorporates herein by reference in its entirety, U.S. Provisional Application Ser. No. 61/783,000, filed Mar. 14, 2013, and entitled "SYSTEM AND METHOD FOR A LAPAROSCOPIC MORCELLATOR."

STATEMENT REGARDING FEDERALLY SPONSORED RESEARCH

This invention was made with United States Government support awarded by the following agencies: National Science Foundation Graduate Research Fellowship Grant No. DGE-1144152. The United States government has certain rights in this invention.

BACKGROUND OF THE INVENTION

Laparoscopy is an increasingly-popular surgical procedure that uses one to five small incisions, each of which is approximately 5-12 millimeters in diameter and extend down, to gain access to an interior surgical site. Each small incision receives a hollow tube or cannula which act as liners to hold the incisions open, thereby providing portals leading down to the interior surgical site. A laparoscopic procedure can then be performed by passing surgical instruments, such as cutting devices, clamps or a viewing apparatus, down the cannulas so that the distal working ends of the instruments can be positioned and used about the surgical site. The proximal handle ends of the instruments remain outside the body where they can be grasped by a surgeon. In some situations, the excised tissue is relatively small and can be passed through the cannula opening, however, in other situations the excised tissue is too large to fit through a cannula intact. In the latter case, the excised tissue must be cut down into a number of smaller pieces before it can be passed through a cannula.

Laparoscopic morcellation is a common method of accomplishing the above described task in the operating room. Further, morcellation also allows many surgeries to be performed laparoscopically, reducing recuperation time and providing cosmetic benefits to patients. Laparoscopic morcellation can be used in surgeries such as hysterectomy, fibroidectomy and myomectomy to remove uteri and uterine fibroids (leiomyomas) through a small abdominal incision. The current standard for the removal of large tissue through a small incision during these surgeries involves grasping tissue and inserting the tissue into a moving cutting tool operating within the body cavity. Some conventional morcellators use blades that are housed in a tube through which the surgeon inserts a tenaculum, grabs part of the tissue, and pulls it through the spinning blades, coring it and aspirating the thin, long piece produced. Other conventional morcellators use bipolar energy to cut the tissue into small pieces that are then removed through laparoscopic ports in a piece-wise manner. A bipolar morcellator applies electricity directly to the tissue through electrodes. The current applied to the tissue causes vaporization and separation of the tissue. Because bipolar morcellators are often inefficient at dissecting large amounts of tissue, they are often used in combination with bladed morcellators.

Unfortunately, the above existing approaches have a number of key limitations; 1) they are time consuming because the devices must be manually moved over the tissue during the cutting step, 2) they do not provide safe containment of tissue during the morcellation process which could lead to seeding (spreading and re-growth) of benign or cancerous tissue, 3) they can lead to accidental damage to surrounding healthy tissue inside the body and 4) the proximity of the morcellator blade to critical structures in the abdomen can result in major morcellation injury to the surrounding tissue, such as a loop of bowel or colon. In addition to these safety risks, current morcellators are inefficient because they operate in a piece-wise or serial manner and the procedure time is highly dependent on tumor size, density, and surgeon skill, thereby prolonging operating time.

Therefore, a laparoscopic morcellator is needed that overcomes the above limitations.

SUMMARY OF THE INVENTION

The present invention relates to a laparoscopic morcellator for cutting and containing tissue during a laparoscopic surgery. It also allows for torque balancing of a retractor mechanism, gas flow regulation of the body cavity, and safety feedback mechanisms that can alert the surgeon. The morcellator is based on an enclosed, motor-actuated mesh, constructed from a plurality of compliant elongate members that apply only an inward-directed cutting force to all of the tissue simultaneously after it has been loaded into a containment mechanism and cutting mechanism combination.

Some embodiments of the invention provide a morcellating device for removing tissue which includes a containment mechanism. The containment mechanism includes an aperture which defines an interior space. The morcellating device also includes a cutting mechanism designed to fit into the interior space of the containment mechanism and a retractor mechanism that is coupled to the cutting mechanism. The morcellating device further includes a motor for actuating the retractor mechanism such that the cutting mechanism constricts and morcellates the tissue.

The cutting mechanism further comprises a perimeter portion and a plurality of compliant elongate members. The plurality of compliant elongate members can form one or more bundles and at least one bundle can extend beyond the perimeter portion of the cutting mechanism. The plurality of compliant elongate members may protrude through the aperture of the containment mechanism to create an opening in the cutting mechanism for receiving the tissue. The containment mechanism comprises a material that is impermeable to tissue and fluid. While the plurality of compliant elongate members comprise a material having an average tension force at break of about 100 Newtons to about 140 Newtons. Further, nodes of the plurality of compliant elongate members are substantially immobile relative to one another upon a force created by deformation of the tissue, whereby the nodes of the plurality of compliant elongate members retain their spacing.

The retracting mechanism of the morcellating device may include a movable member coupled to one or more of the bundles that may be controlled by a foot actuator or a hand actuator. In one embodiment, the morcellating device may include a dynamic torque balancing mechanism that includes a first secondary motor coupled to a first movable member and a second secondary motor coupled to a second movable member, such that the tissue has a center of mass.

The dynamic torque balancing mechanism may further include an accelerometer coupled to the first and second secondary motors, such that when the torque is above a specific threshold on either the first movable member or the second movable member, the bundles coupled to either the first or second movable members are pulled by either the first or second secondary motor to center the center of mass of the tissue over an inside surface of the a hollow shaft, thereby providing a counter balance.

Alternatively, the morcellating device may include a static torque balancing mechanism. The static torque balancing mechanism may include a hollow shaft having an axis of rotation, and a torque shaft coupled to the motor and the retractor mechanism. The retractor mechanism may include a first moveable member and a second moveable member, such that actuation of the retractor mechanism activates the motor and the first and second movable members rotate in opposite directions, thereby reducing the overall torque of the first and second movable member.

The morcellating device may also include a housing which includes a handle and an actuator. The housing encloses the movable member, the actuator coupled to the motor such that when the actuator is pressed, the motor is activated, thereby activating the retractor mechanism and allowing the movable member to provide a retracting force to the bundles. The housing, including the handle, is configured to be opened and designed for insertion of replaceable parts. In addition, the handle may be configured to be opened and the plurality of compliant elongate members disengaged from the movable member and a new set of compliant elongate members can be coupled to the movable member, thereby making at least a portion of the morcellating device reusable.

The morcellating device may further include a deployment mechanism that houses the cutting mechanism and the containment mechanism. The deployment mechanism is separate from the housing for deployment of the cutting mechanism and the containment mechanism into a body. A seal may be coupled to the housing to inhibit the tissue from contaminating the motor and the retractor mechanism. In addition, a coupling member can be coupled to the motor and engage the retractor mechanism. The motor and the coupling member may be positioned to avoid contact with tissue or fluids in the body, and a flexible tube may be disposed between the coupling member and the housing.

The retractor mechanism may be coupled to a hollow shaft that is dimensioned to surround a portion of the cutting mechanism. The hollow shaft may be partially hollow and coupled to a support block that is coupled to the movable member. The hollow shaft has at least one of a chamfered end portion, a flared end portion, or a lubricated end portion thereby reducing damage of the containment mechanism and the cutting mechanism as the containment mechanism and the cutting mechanism are pulled through the hollow shaft. The containment mechanism and the cutting mechanism may have a retracted position and an extended position. In the retracted position, the aperture of the containment mechanism is coupled to an outer surface of the hollow shaft, the cutting mechanism is coupled to the inside of the containment mechanism, and a portion of the containment mechanism is disposed within an inner space of the hollow shaft. In the extended position, the aperture of the containment mechanism is coupled to the outer surface of the hollow shaft, the cutting mechanism is coupled to the inside of the containment mechanism, and the containment mechanism is disposed external to the inner space of the hollow shaft.

In another embodiment, the containment mechanism and the cutting mechanism have a retracted position and an extended position, such that in the retracted position, the aperture of the containment mechanism is coupled to an inner surface of the hollow shaft, the cutting mechanism is coupled to the inside of the containment mechanism, and the containment mechanism is disposed within the inner space of the hollow shaft. In the extended position, the aperture of the containment mechanism is coupled to the inner surface of the hollow shaft, the cutting mechanism is coupled to the inside of the containment mechanism, and the containment mechanism is disposed external to the inner space of the hollow shaft.

The hollow shaft may be removable from the morcellating device or may be configured to be opened, thereby allowing removal of tissue. The hollow shaft may be coupled with threads to the housing of the morcellating device to secure the hollow shaft to the morcellating device. In addition, the containment mechanism may further comprise a closing mechanism for closing the aperture of the containment mechanism about an outer portion of the hollow shaft, such that the closing mechanism is voluminous to capture the tissue. The morcellating device may further include a gas flow control element coupled to the hollow shaft for controlling the flow of gas through the hollow shaft and the morcellating device.

In one embodiment, the morcellating device may include a controller in electrical communication with the motor and a sensor in electrical communication with the controller. The sensor senses load variations on the retractor mechanism, such that when the sensor senses a specific load threshold, the controller automatically stops motion of the motor, thereby stopping motion of the containment mechanism and cutting mechanism. The controller may be configured to decrease a speed of rotation of the motor and the retractor mechanism when the sensor senses a load below the specific load threshold. Similarly, the controller may also be configured to increase the speed of rotation of the motor and the retractor mechanism when the sensor senses a load above the specific load threshold.

The morcellating device may also include a controller in electrical communication with the motor and a sensor in electrical communication with the controller. The sensor senses when the cutting mechanism is inside the hollow shaft which is coupled to the retractor mechanism, such that when the sensor senses the cutting mechanism is fully within an inner portion of the hollow shaft, the controller automatically stops motion of the motor, thereby stopping motion of the cutting mechanism. Further, the morecellating device may include an indicator that indicates a specific position of the hollow shaft within a trocar and a sensor in electrical communication with the indicator. The sensor senses how far the hollow shaft, which is coupled to the retractor mechanism, extends into the trocar, such that when the sensor senses the hollow shaft is inside the trocar at a specific distance, the indicator automatically alerts a user. An insertion device, which may be flexible and/or inflatable, may be used to insert the containment mechanism into the trocar The morcellating device may further include a support for externally supporting the morcellating device. The morcellating device may be configured for use in a robotic surgery. Further, the motor of the morcellating device may be off-board of the housing that encloses a part of the retractor mechanism. The morcellating device may include a second motor coupled to the containment mechanism for removal of the containment mechanism from the body. Alternatively, a pulling device may be coupled to the containment mechanism and configured to be hand activated for removal of the containment mechanism from the body. Or, a mechanical device, which may be pneumatic, may be coupled to the containment mechanism for removal of the containment mechanism from a patient body. Further, a vibrator mechanism may be coupled to the cutting mechanism, thereby vibrating the cutting mechanism while the retractor mechanism retracts the cutting mechanism.

In another embodiment, the invention provides a tissue removal device for removing tissue which includes a containment mechanism with an aperture, a retractor mechanism coupled to the containment mechanism, and a motor. The containment mechanism is dimensioned to surround at least a part of the tissue and the motor actuates the retractor mechanism such that the containment mechanism constricts the tissue.

The tissue removal device may further include a closing device for closing the aperture of the containment mechanism. The containment mechanism comprises a material that is impermeable to tissue and fluid, and the aperture of the containment mechanism may be configured to receive the tissue. The closing device may be being positioned on a perimeter portion of the containment mechanism to capture the tissue. In addition, the retractor mechanism of the tissue removal device may include a movable member coupled to the containment mechanism. The retractor mechanism may be controlled by a foot actuator or a hand actuator. Further, a housing of the tissue removal device may include a handle and an actuator. The housing encloses the movable member, the actuator coupled to the motor such that when the actuator is pressed, the motor is activated, thereby activating the retractor mechanism and allowing the movable member to provide a retracting force on the containment mechanism. In one embodiment, the housing, including the handle, is configured to be opened and designed for insertion of replaceable parts.

A deployment mechanism that houses the containment mechanism may be separate from the housing for deployment of the containment mechanism into a body. A seal may be coupled to the housing to inhibit the tissue from contaminating the motor and the retractor mechanism. The retractor mechanism may be engaged by a coupling member that is coupled to the motor. The motor and the coupling member are positioned to avoid contact with tissue or fluids. In addition, a flexible tube may be disposed between the coupling member and the housing. A support block may be coupled to a hollow shaft, which is coupled to the retractor mechanism, and the moveable member.

The hollow shaft may be dimensioned to surround a portion of the containment mechanism, and the hollow shaft may be partially hollow. The hollow shaft may be removable from the tissue removal device or is configured to be opened, thereby allowing removal of tissue. In one form, the hollow shaft is coupled with threads to a housing of the tissue removal device, thereby securing the hollow shaft to the tissue removal device. The hollow shaft may have at least one of a chamfered end portion, a flared end portion, and a lubricated end portion thereby reducing damage of the containment mechanism as it is pulled through the hollow shaft.

The containment mechanism has a retracted position and an extended position. In the retracted position, the aperture of the containment mechanism is coupled to an outer surface of the hollow shaft, and a portion of the containment mechanism is disposed within an inner space of the hollow shaft. In the extended position, the aperture of the containment mechanism is coupled to the outer surface of the hollow shaft, and the containment mechanism is disposed external to the inner space of the hollow shaft. In another form, the containment mechanism has a retracted position and an extended position, such that in the retracted position, the aperture of the containment mechanism is coupled to an inner surface of the hollow shaft and the containment mechanism is disposed within the inner surface of the hollow shaft. In the extended position, the aperture of the containment mechanism is coupled to an inner surface of the hollow shaft and the containment mechanism is disposed external to the inner space of the hollow shaft.

In one embodiment, the tissue removal device may include a controller in electrical communication with the motor and a sensor in electrical communication with the controller. The sensor senses load variations on the retractor mechanism, such that when the sensor senses a specific load threshold, the controller automatically stops motion of the motor, thereby stopping motion of the containment mechanism. The controller may be configured to decrease a speed of rotation of the motor and the retractor mechanism when the sensor senses a load below the specific load threshold. Similarly, the controller may also be configured to increase the speed of rotation of the motor and the retractor mechanism when the sensor senses a load above the specific load threshold.

The tissue removal device may also include an indicator that indicates a specific distance of the hollow shaft within a trocar and a sensor in electrical communication with the indicator. The sensor senses how far the hollow shaft, which is coupled to the retractor mechanism, extends into the trocar, such that when the sensor senses the hollow shaft is inside the trocar at a specific distance, the indicator automatically alerts a user. The tissue removal device may further include a gas flow control element coupled to the hollow shaft for controlling the flow of gas through the hollow shaft and the tissue removal device. In addition, an insertion device, which may be flexible and/or inflateable, may be used to insert the containment mechanism into the trocar.

The tissue removal device may further include a mechanism for externally supporting the tissue removal device. The tissue removal device may be configured for use in a robotic surgery. Further, the motor of the tissue removal device may be off-board of the housing that encloses a part of the retractor mechanism. The tissue removal device may include a pulling device that may be coupled to the containment mechanism and configured to be hand activated for removal of the containment mechanism from the body. Or, a mechanical device, which may be pneumatic, may be coupled to the containment mechanism for removal of the containment mechanism from a patient body.

In another embodiment, the invention provides a tissue removal device for removing tissue. The tissue removal device includes a cutting mechanism comprised of a wire loop and dimensioned to surround at least a part of the tissue. The tissue removal device also includes a retractor mechanism coupled to the cutting mechanism and a motor for actuating the retractor such that the cutting mechanism constricts and severs the tissue.

In another embodiment, the invention provides a method for removal of tissue using a morcellating device. The method involves providing a containment mechanism having an aperture and providing a cutting mechanism coupled to an interior of the containment mechanism. The cutting mechanism is also coupled to a retractor mechanism that is activatable by a motor. The method further involves surrounding the tissue with the cutting mechanism and the containment mechanism and then closing the aperture of the containment mechanism. The aperture of the containment mechanism may be closed through magnetism, mechanically, or with a tool. The motor is then activated to actuate the retractor mechanism such that the cutting mechanism constricts and creates morcellated tissue. The morcellated tissue is contained in the containment device.

In yet another embodiment, the invention provides a method for removal of tissue by providing a containment mechanism including an aperture and providing a retractor mechanism coupled to the containment mechanism. The tissue is then surrounded with the containment mechanism and the aperture of the containment mechanism is closed. The containment mechanism may be closed through magnetism, mechanically, or with a tool A motor is activated which actuates the retractor mechanism such that the containment mechanism constricts the tissue and the tissue in contained in the containment device.

These and other features, aspects, and advantages of the present invention will become better understood upon consideration of the following detailed description, drawings, and appended claims.

BRIEF DESCRIPTION OF THE DRAWINGS

FIG. 7 is a side cross-sectional view of the morcellating device with the cutting mechanism and containment mechanism attached to an inner surface of a hollow shaft in a retracted position.

FIG. 8 is a side cross-sectional view of the morcellating device with the cutting mechanism and containment mechanism partially deployed from the hollow shaft of FIG. 7 in an extended position.

FIG. 9 is a side cross-sectional view of the morcellating device with the cutting mechanism and the containment mechanism surrounding the tissue and deployed from the hollow shaft with the containment mechanism surrounding only the outer portion of the hollow shaft of FIG. 8.

FIG. 10 is a side cross-sectional view of the morcellating device with the cutting mechanism constricting the tissue of FIG. 9.

FIG. 11 is a side cross-sectional view of the morcellating device with the cutting mechanism morcellating the tissue of FIG. 10.

FIG. 12 is a partial perspective view of the morcellating device with the cutting mechanism and the containment mechanism attached to the inner surface of the hollow shaft in the retracted position according to another embodiment of the present invention.

FIG. 13 is a side cross-sectional view of the morcellating device with the cutting mechanism and the containment mechanism attached to the inner surface of the hollow shaft in the retracted position of FIG. 12.

FIG. 14 is a side cross-sectional view of the cutting mechanism and the containment mechanism of FIG. 13 deployed from the hollow shaft in the extended position.

FIG. 15 is a perspective view of the cutting mechanism and the containment mechanism deployed from the hollow shaft with the containment mechanism surrounding an outer surface of the hollow shaft in the extended position of FIG. 14.

FIG. 16 is a perspective view of the cutting mechanism surrounded by the containment mechanism in an open position.

FIG. 17 is a perspective view of the cutting mechanism surrounded by the containment mechanism in a closed position.

DETAILED DESCRIPTION OF THE INVENTION

Figure 1:
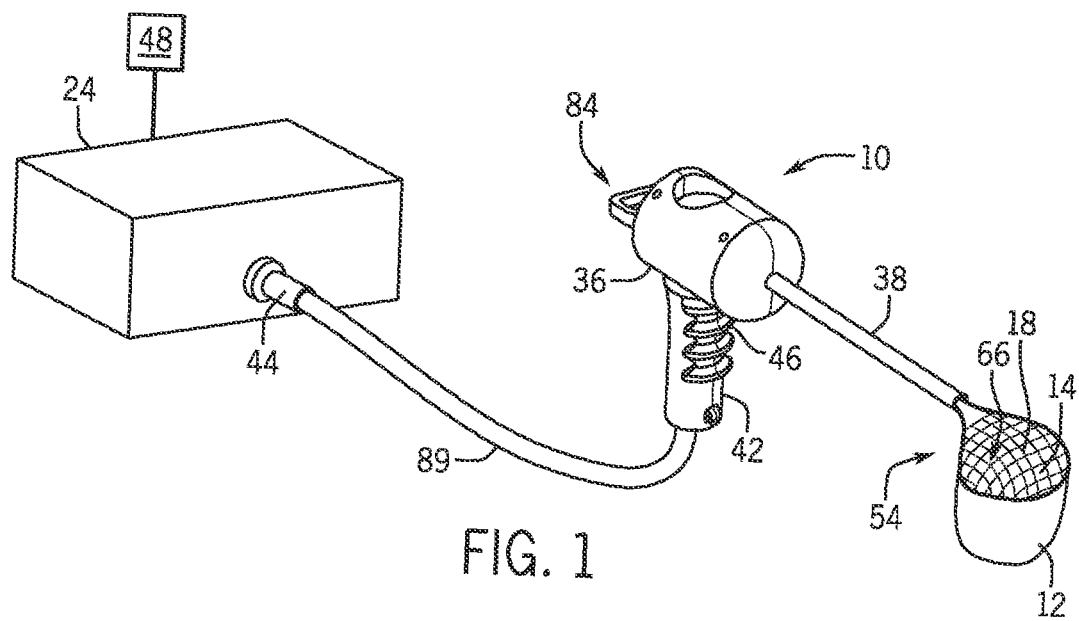
FIG. 1 is a perspective view of an example laparoscopic morcellating device according to one embodiment of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Figure 2:
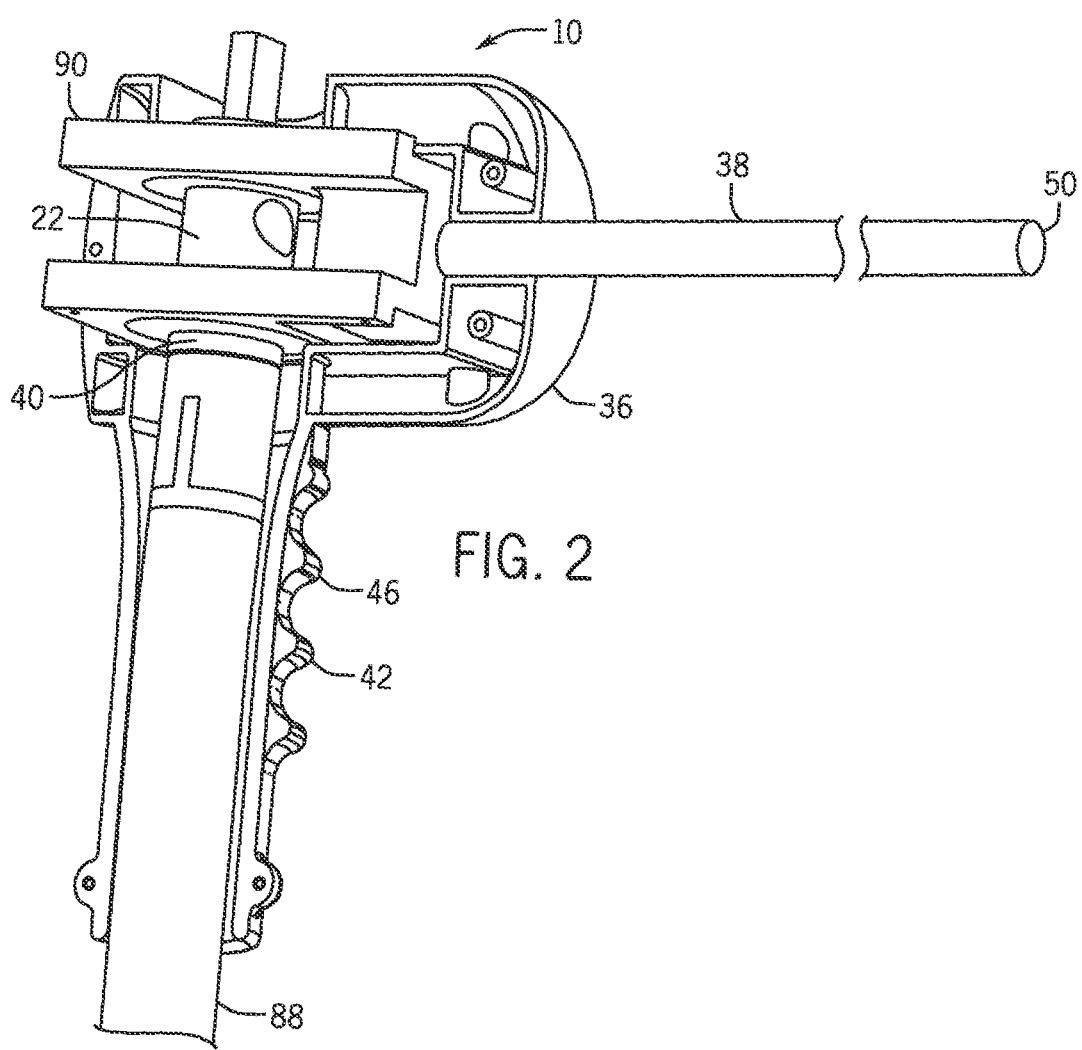
FIG. 2 is a detailed side perspective view of the morcellating device of FIG. 1 with one shell of the housing removed.
Figure 6:
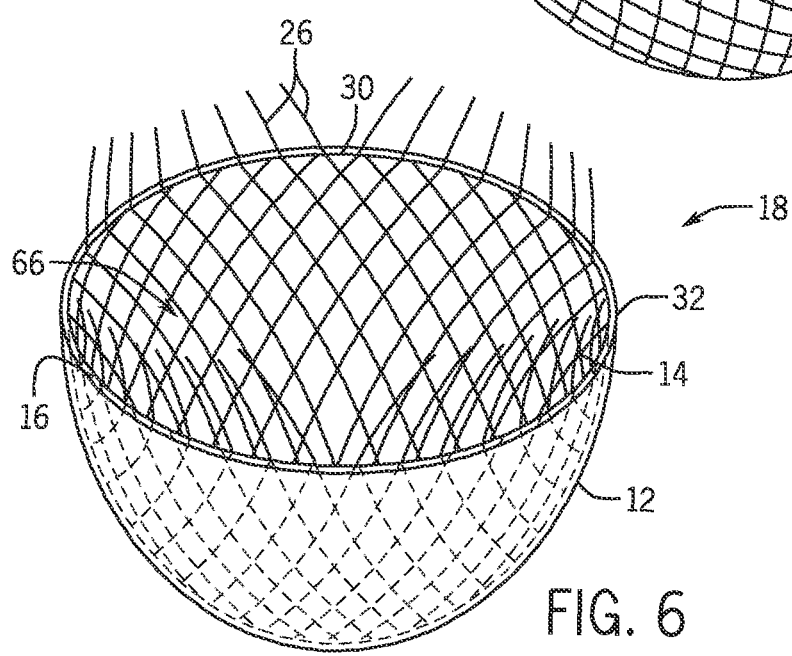
FIG. 6 is a side perspective view of the cutting mechanism of FIG. 5 surrounded by a containment mechanism.

FIG. 1 illustrates an example morcellating device 10 coupled to a motor 24 by a coupling member 44 and a flexible tube 89 which is coupled to a torque shaft 88 (see FIG. 2). The coupling member 44 is coupled to the motor 24 and engages a retractor mechanism 22 (see FIG. 7). The morcellating device 10 further includes a housing 36 with a handle 42. Best shown in FIGS. 2 and 3, the housing 36 holds a portion of the flexible tube 89 and torque shaft 88, which is coupled to a movable member 40, a support block 90 and a hollow shaft 38. Extending from the hollow shaft 38 is a cutting mechanism 18 with an aperture 14 that is dimensioned to fit into an interior space 16 of a containment mechanism 12 as shown in FIG. 6. The cutting mechanism 18 and the containment mechanism 12 combination includes an opening 66 through which tissue 98 can be placed, as shown in FIG. 9. The morcellating device 10 further includes the retractor mechanism 22, shown in FIG. 7. The retractor mechanism 22 includes bundles 34 wound around the movable member 40, such that when the torque shaft 88 is activated by the motor 24, the movable member 40 rotates and the cutting mechanism 18 retracts into the hollow shaft 38 and morcellates the tissue 98.

Figure 3:
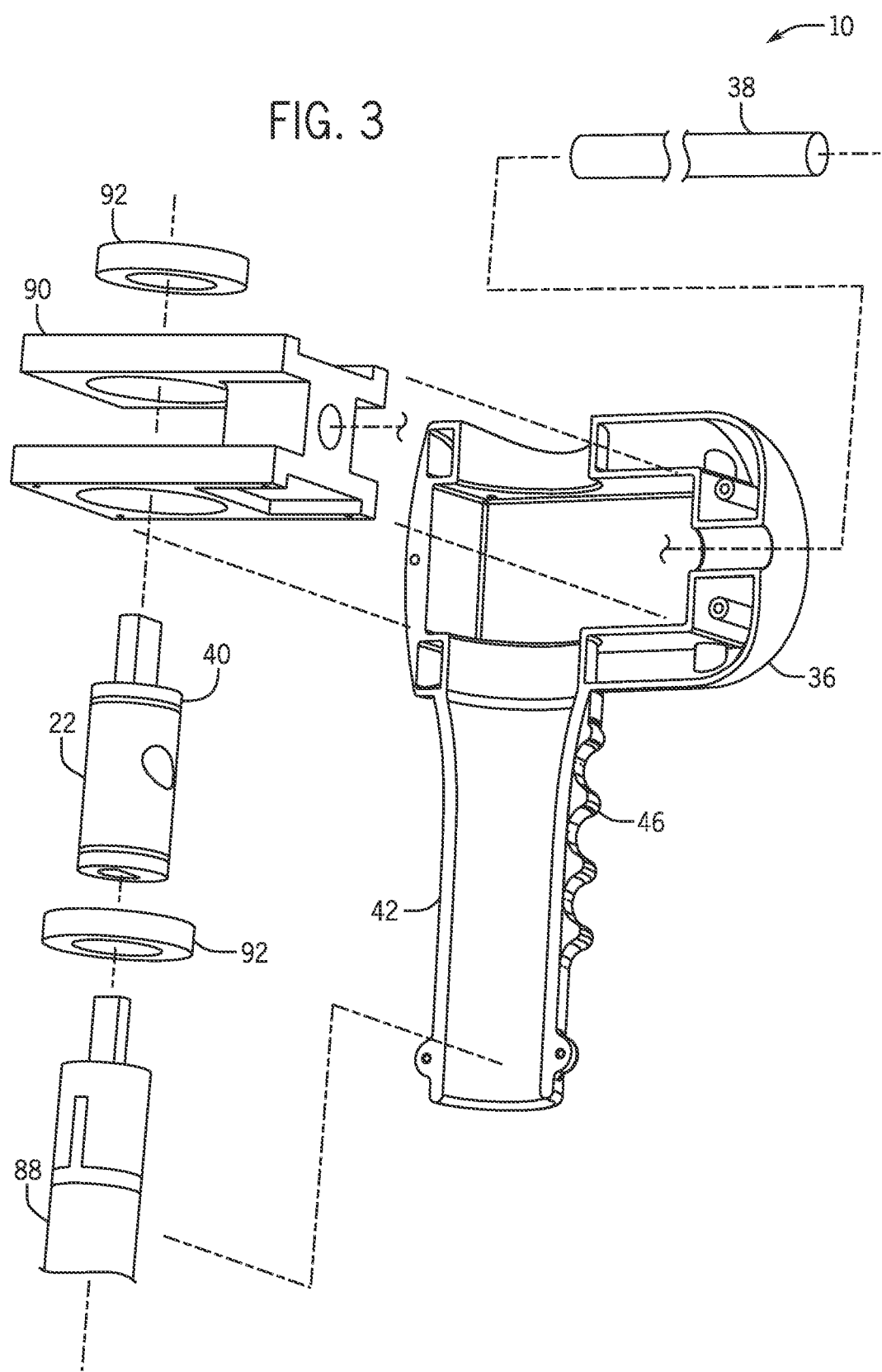
FIG. 3 an exploded view of the morcellating device of FIG. 2.

Turning now to FIGS. 2 and 3, the housing 36 can be made of a material that is lightweight and includes a handle 42 having an ergonomic grip. The housing 36 material is sufficiently strong to support a load on the movable member 40, to which the bundles 34 of the cutting mechanism 18 are attached, and the hollow shaft 38 that is created by the tissue 98 placed in the interior space 16 of the cutting mechanism 18 and the containment mechanism 12. The housing 36 may be opened by a sliding mechanism, hinges, or some type of mechanism to facilitate the replacement of the torque shaft 88, the movable member 40, the plurality of compliant elongate members 26, the support block 90, the bearings 92 and/or the hollow shaft 38, making the housing 36 of the morcellating device 10 capable of receiving replaceable parts (not shown). The housing 36 and/or the hollow shaft 38 can be sealed relative to the torque shaft 88 to avoid contamination from fluid and the tissue 98. Further, the housing 36 can be sealed to inhibit gas leakage from the abdomen, as will be described in further detail below.

As best shown in FIGS. 2 and 3, the retractor mechanism 22 includes the torque shaft 88 coupled to the movable member 40, and the movable member 40 coupled to the support block 90. The support block 90 further includes two press fit bearings 92 which surround both ends of the movable member 40. Also coupled to the support block 90 is the hollow shaft 38. The above described configuration represents the retractor mechanism 22 along with the bundles 34 of the cutting mechanism 18 wrapped around the movable member 40, as shown in FIGS. 7-11.

The motor 24 of the morcellating device 10, as shown in FIG. 1, further includes an actuator 46 positioned on the handle 42 and coupled to the motor 24. Alternatively, the actuator 46 which controls the retractor mechanism 22 can be controlled by a user's foot. In the preferred embodiment, the actuator 46 can be a trigger or button type mechanism positioned on the handle 42, such that when the actuator 46 is pressed by the user, the motor 24 is automatically activated. Activation of the motor 24 causes the retractor mechanism 22 to become activated and torque is transmitted to the movable member 40 causing it to rotate. Rotation of the movable member 40 provides a retracting force to the bundles 34 of the cutting mechanism 18 and the bundles 34 wind around the rotating movable member 40. The movable member 40 preferably rotates at a frequency of approximately 8 RPM, and the rotation frequency of the motor 24 is preferably around 8 RPM for simplicity. Optionally, the motor 24 can have a rotation frequency greater than 8 RPM which can be reduced, so that the movable member 40 rotates at a frequency of approximately 8 RPM.

In the preferred embodiment, the motor 24 is off-board the morcellating device 10. Alternatively, the motor 24 can be on-board the morcellating device 10 (not shown), however an on-board motor 24 would make the morcellating device 10 heavier and possibly more difficult for the user to operate. Whether an on-board or off-board motor 24 is used, the motor 24 serves as a force generation device which can transmit power pneumatically, hydraulically, electrically or in a similar fashion. The motor 24 can be a split phase parallel shaft gear motor that can satisfy the torque and speed requirements to morcellate the tissue 98. However, a smaller motor 24 could be used in conjunction with a worm-gear reduction (not shown) positioned on the housing 36 of the morcellating device 10. Torque transmission from the motor 24 to the worm-gear can be achieved by a flexible driveshaft connected between the motor 24 and the movable member 40, or, alternatively, gear reductions connected to the end of the flexible driveshaft. Further, to support the morcellating device 10 with either an on-board or off-board motor 24, a support (not shown), such as a tripod or wires suspended from a ceiling or other structure could be used.

Figure 18:
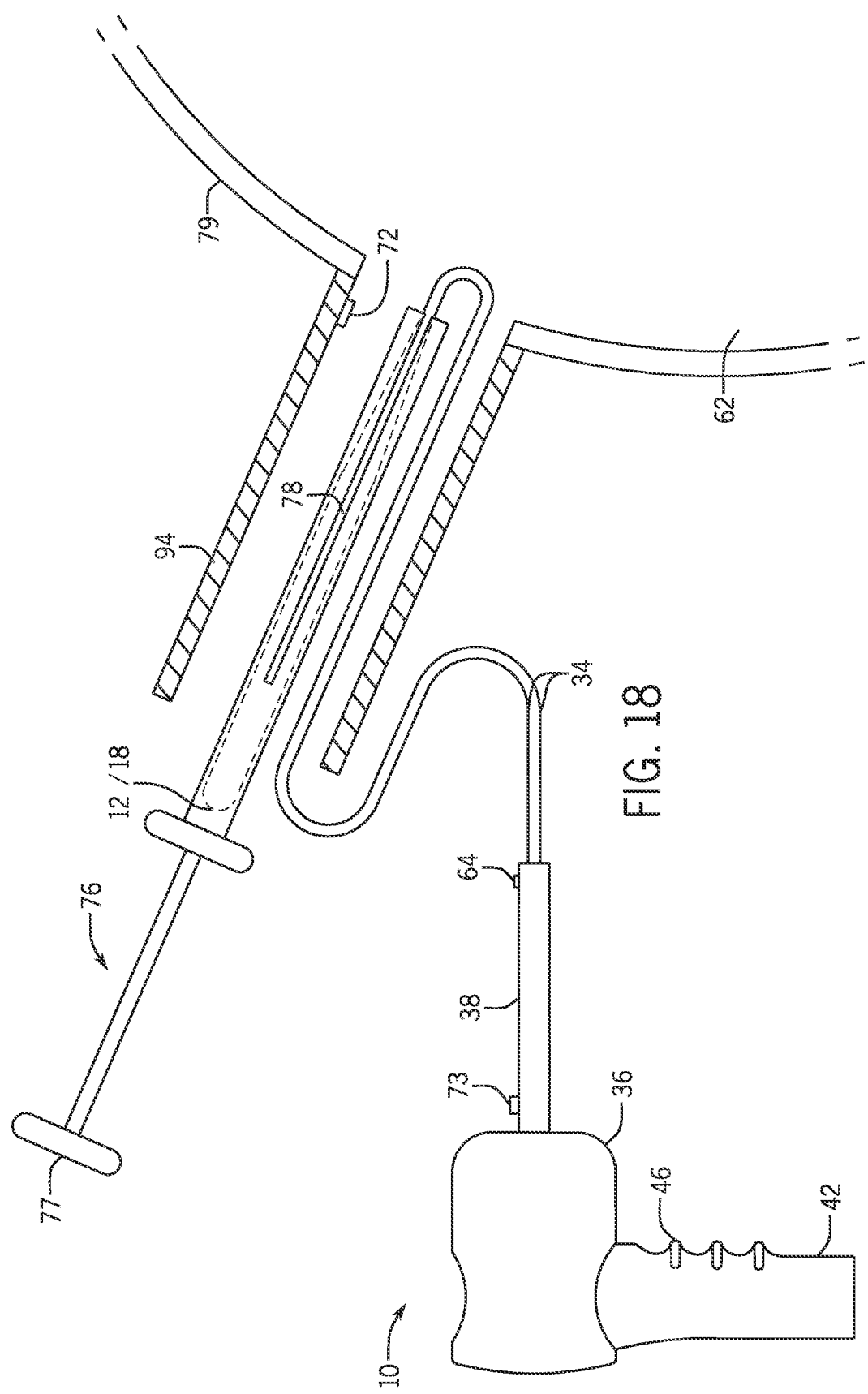
FIG. 18 is a side perspective view of a deployment mechanism for the cutting mechanism and the containment mechanism.

Turning now to FIGS. 12 and 13, the hollow shaft 38 includes an outer surface 56, an inner surface 58 and an inner space 60. The inner space 60 of the hollow shaft 38 can be partially hollow, such that the hollow shaft 38 is dimensioned to surround a portion of the cutting mechanism 18. The distal end of the hollow shaft 38 can be threadly coupled to the support block 90, as shown in FIG. 3. The inner space 60 of the hollow shaft 38 is where the cutting mechanism 18, which is dimensioned to fit into the containment mechanism 12, is placed prior to deploying into the body 79 of a patient, as shown in FIG. 18. The hollow shaft 38 is cylindrical in shape and can be between 12-15 centimeters in length. A hollow shaft 38 that is greater than 15 centimeters in length can be used alternatively for obese patients. The hollow shaft 38 can be constructed of stainless steel and the hollow shaft 38 can have an outer diameter that is smaller than the diameter of a trocar 94, as shown in FIG. 18. Thus, the smaller outer diameter of the hollow shaft 38 allows clearance for a perimeter portion 32 of the containment mechanism 12 to be secured around an outer surface 56 of the hollow shaft 38, as shown in FIG. 8, or a part of the perimeter portion 32 of the containment mechanism 12 to be disposed on an inner surface 58 of the hollow shaft 38, as shown in FIG. 7, as the hollow shaft 38 is inserted or removed from the trocar 94. The hollow shaft 38 can further include an end portion 50 which serves as a tissue cutting surface. The end portion 50 of the hollow shaft 38 can be chamfered, flared or lubricated to assist deployment of the cutting mechanism 18 and containment mechanism 12 combination into the body 79. The end portion 50 may also assist in retracting the cutting mechanism 18, with the tissue 98 positioned in the interior space 16 of the cutting mechanism 18, into the hollow shaft 38, thereby reducing damage of the cutting mechanism 18 and containment mechanism 12 combination.

Alternatively, the hollow shaft 38 could include a magnetic lining disposed on the outer surface 56 of the hollow shaft 38 which would be constructed of a non-magnetic material. Or, the hollow shaft 38 could include a non-magnetic lining disposed on the inner surface 58 of the hollow shaft 38 which would be constructed of a magnetic material. Both of the above mentioned alternatives would assist in guiding a closing mechanism 74, as well as assist in providing adhesion of the perimeter portion 32 of the containment mechanism 12 to an outer surface 56 of the hollow shaft 38, as shown in FIG. 8 or ensuring the perimeter portion 32 is disposed on an inner surface 58 of the hollow shaft 38, as shown in FIG. 7.

Figure 4:
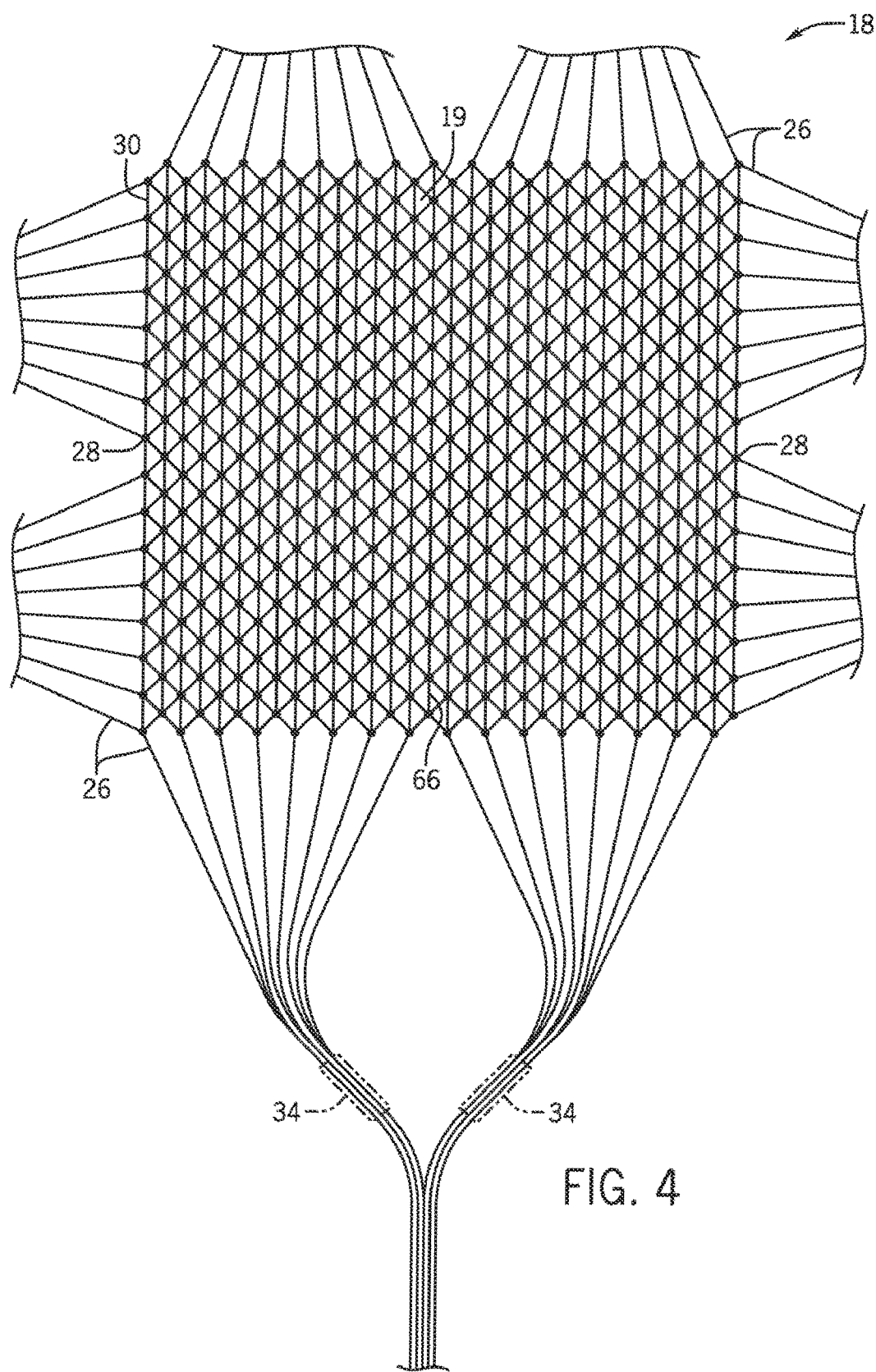
FIG. 4 is a top perspective view of a plurality of compliant elongate members forming a cutting mechanism used to cut tissue in the device of FIG. 1.
Figure 5:
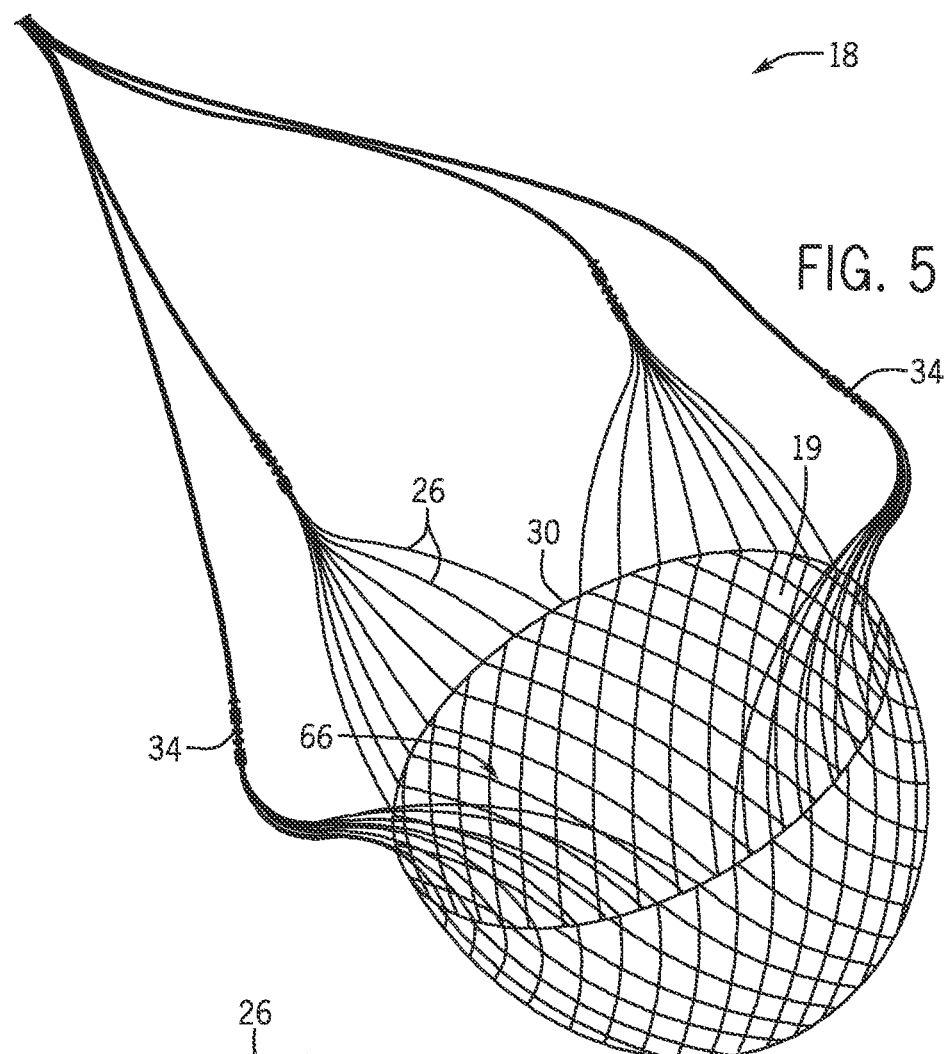
FIG. 5 is a perspective view of the plurality of compliant elongate members of FIG. 4 forming separate bundles.

Turning now to FIGS. 4 and 5, the cutting mechanism 18 comprises a plurality of compliant elongate members 26 and a cutting area 19 to morcellate the tissue 98. The plurality of compliant elongate members 26 are bladeless and should have less than a $^{12}/_{1,000}$ inch gauge and preferably have an average tension force at break of about 100 N to about 140 N. The plurality of compliant elongate members 26 are collected into bundles 34 at a perimeter portion 30 of the cutting mechanism 18. The perimeter portion 30 of the cutting mechanism 18 defines an opening 66 for receiving tissue 98. The plurality of compliant elongate members 26 that extend beyond the perimeter portion 30 into the bundles 34 do not cut the tissue 98. Rather, the bundles 34 extend through the hollow shaft 38, as shown in FIG. 7, and are coupled to the movable member 40. In the preferred embodiment, the cutting mechanism 18 is constructed of plastic, such as Kevlar, high-density polyethylene (HDPE) fishing line or nylon fishing line, however any metal or non-metal material can be used as an alternative. The plurality of compliant elongate members 26 that extend below the perimeter portion 30 of the cutting mechanism 18 defines the cutting area 19. The cutting area 19 can be in the form of an open weave or knotted, such that each of the plurality of compliant elongate members 26 intersect at a node 28, forming a grid of squares, regular or irregular, or any other shape. The nodes 28 are substantially immobile relative to one another upon an inward force F, shown in FIG. 10, created by the deformation of the tissue 98, whereby the nodes 28 of the plurality of compliant elongate members 26 retain their spacing. Because the cutting mechanism 18 applies only an inward directed cutting force F, the need for manipulating sharp tools or devices inside the body 79 is eliminated. Each square formed in the cutting area 19 can have a length between 3 millimeters and 2 centimeters in order to fit the industry standard of pathology cassettes. The cutting area 19 should be about 20 inches by 20 inches.

Turning now to FIGS. 6, 16 and 17, the cutting mechanism 18 is dimensioned to fit into the interior space 16 of the containment mechanism 12, such that it lines the containment mechanism 12. The cutting mechanism 18 can be attached at multiple points to the containment mechanism 12, so that the cutting mechanism 18 does not move around and make it difficult to ensure the tissue 98 is completely placed in the interior space 16 of the containment mechanism 12. Having the cutting mechanism 18 removably attached at multiple points to the containment mechanism 12 allows the cutting mechanism 18 to detach from the containment mechanism 12 when the cutting mechanism 18 is being retracted into the hollow shaft 38 by the retractor mechanism 22, as shown in FIGS. 10 and 11, allows for the containment mechanism 12 to be left inside the body 79. Further, the cutting mechanism 18 can be colored so that it is more visible on the endoscope and the cutting mechanism 18 can be coated with a lubricant or anti-coagulant to decrease the friction as it enters the hollow shaft 38, as well as prevent the tissue 98 from sticking to the cutting mechanism 18.

As previously described, the containment mechanism 12 is dimensioned to encapsulate the cutting mechanism 18, as shown in FIG. 16. The containment mechanism 12 can be a standard surgical retrieval bag with the closing mechanism 74 that is threaded through the perimeter portion 32 of the containment mechanism 12, best shown in FIGS. 16 and 17. The closing mechanism 74 is a drawstring-like mechanism that when pulled, seals the perimeter portion 32 around the outer surface 56 of the hollow shaft 38 once the tissue 98 is placed into the interior space 16 of the containment mechanism 12, as shown in FIGS. 9 and 15. Alternatively, the closing mechanism 74 could be a flexible loop, a plurality of strings, a sliding fit inside a sheath, or any other mechanism. Sealing the containment mechanism 12 around the outer surface 56 of the hollow shaft 38 can prevent seeding, which may occur when tissue 98 spills into the body 79 of the patient. For malignant and premalignant tissue 98, the seal between the containment mechanism 12 and the outer surface 56 of the hollow shaft 38 is critical, and the containment mechanism 12 should be impermeable to fluid and the cells of the tissue 98 contained within the interior space 16. Further, the containment mechanism 12 can have an aperture 14 with a diameter of about 5.5 inches, a length of about 11.1 inches, and a volume of about 3,000 milliliters. The containment mechanism 12 can be constructed from a rip-stop nylon to help prevent any tearing that may occur during surgery.

Turning now to FIG. 7, the morcellating device 10 is used during a laparoscopic procedure in order to remove tissue 98 from the body 79. To begin, the bundles 34 of the cutting mechanism 18 are coupled to the movable member 40. As previously described, the cutting mechanism 18 is coupled to and encapsulated within the interior space 16 of the containment mechanism 12, as shown in FIG. 8. The cutting mechanism may be inserted into the inner space 60 of the hollow shaft 38, such that the morcellating device 10 is in the retracted position 52, as shown in FIG. 7. In one embodiment, a perimeter portion 32 of the containment mechanism 12 can be coupled to the inner surface 58 of the hollow shaft 38. Similarly, a perimeter portion 30 of the cutting mechanism 18 is coupled to the inner surface 58 of the hollow shaft 38.

An alternative retracted position 52 is shown in FIG. 8 and described below, where the containment mechanism 12 is lightly coupled to the outer surface 56 of the hollow shaft 38, and the cutting mechanism 18 is coupled to the interior space 16 of the containment mechanism 12. The perimeter portions 30, 32 of the cutting mechanism 18 and the containment mechanism 12 are attached to the hollow shaft 38 as described above in order to allow the tissue 98 to be placed into the interior space 16 of the containment mechanism 12 through the opening 66, as shown in FIG. 5. The morcellating device 10 is inserted into the trocar 94 of FIG. 18, and the containment mechanism 12 and cutting mechanism 18 combination are deployed into the external environment 62, such that the morcellating device 10 is in the extended position 54, as shown in FIG. 9.

Deployment of the containment mechanism 12 and cutting mechanism 18 combination into the external environment 62 can be achieved by a spring load mechanism (not shown), by pulling it with a tenaculum (not shown) and opening it, or with a deployment mechanism 76, shown in FIG. 18. Deployment of the containment mechanism 12 and cutting mechanism 18 combination using the deployment mechanism 76 will be described in detail below. Prior to deployment, an insertion device (not shown) that is coaxial with the hollow shaft 38 can be used to insert the containment mechanism 12 and cutting mechanism 18 combination into the hollow shaft 38. The insertion device 75 can be flexible and/or inflatable.

Once the morcellating device 10 is in the extended position, as shown in FIG. 9, the tissue 98 is placed into the interior space 16 of the containment mechanism 12 through the opening 66. A tool, such as a tenaculum (not shown) can then be used to grasp the perimeter portion 32 of the containment mechanism 12, which may have been previously attached to the inner surface 58 of the hollow shaft 38, as shown in FIG. 7, and position the perimeter portion 32 around the entire outer surface 56 of the end portion 50 of the hollow shaft 38 as shown in FIG. 9. The closing mechanism 74 is then pulled by the user to seal the containment mechanism 12 around the outer surface 56 of the end portion 50. The user can then activate the retractor mechanism 22 by pressing the actuator 46. Rotation of the retractor mechanism 22 will wind the bundles 34 of the cutting mechanism 18 around the movable member 40 and begin to constrict the tissue 98 as shown in FIG. 10. Optionally, a vibrator (not shown) can be coupled to the cutting mechanism 18 to vibrate the cutting mechanism 18 as it is retracted by the retractor mechanism 22.

As the user continues to press the actuator 46, the bundles 34 continue to wind around the movable member 40 until the cutting mechanism 18 constricts the tissue 98 against the end portion 50 of hollow shaft 38. Because the tissue 98 is too large to fit through the end portion 50 of the hollow shaft 38, the cutting area 19 of the cutting mechanism 18 morcellates the tissue 98 into morcellated tissue 100, as shown in FIG. 11. The smaller portions of the morcellated tissue 100 will then drop into the containment mechanism 12. The morcellating device 10 is then removed from the trocar 94 and the morcellated tissue 100 is aspirated out of the containment mechanism 12. The hollow shaft 38 is disconnected from the housing 36 and the remaining morcellated tissue 100 is recovered from the cutting mechanism 18.

In another embodiment, as shown in FIGS. 8 and 12-15, the cutting mechanism 18 is encapsulated in the interior space of 16 of the containment mechanism 12 and inserted into the inner space 60 of the hollow shaft 38, such that the morcellating device 10 is in the retracted position 52. The perimeter portion 32 of the containment mechanism 12 is attached only to the inner surface 58 of the hollow shaft 38. Similarly, a perimeter portion 30 of the cutting mechanism 18 is attached the inner surface 58 of the hollow shaft 38. The morcellating device 10 is inserted into the trocar 94 of FIG. 18, and the containment mechanism 12 and cutting mechanism 18 combination are deployed into the external environment 62, such that the morcellating device 10 is in the extended position 54, as shown in FIG. 14. Similar to the previous embodiment, once the morcellating device 10 is in the extended position 54, a tool, such as a tenaculum (not shown) can then be used to grasp the perimeter portion 32 of the containment mechanism 12, which was previously attached to the entire inner surface 58 of the hollow shaft 38, and position the perimeter portion 32 around the entire outer surface 56 of the end portion 50 of the hollow shaft 38 as shown in FIGS. 9 and 15.

Prior to coupling the perimeter portion 32 of the containment mechanism 12 to the entire outer surface 56 of the hollow shaft 38, the tissue 98 is placed into the interior space 16 of the containment mechanism 12 through the opening 66. The closing mechanism 74 is then pulled by the user to seal the containment mechanism 12 around the outer surface 56 of the end portion 50. The user can then activate the retractor mechanism 22 by pressing the actuator 46. Rotation of the retractor mechanism 22 will wind the bundles 34 of the cutting mechanism around the movable member 40 and begin to constrict the tissue 98 as shown in FIG. 10. As the user continues to press the actuator 46, the bundles 34 continue to wind around the movable member 40 until the cutting mechanism 18 constricts the tissue 98 against the end portion 50 of hollow shaft 38. Because the tissue 98 is too large to fit through the end portion 50 of the hollow shaft 38, the cutting area 19 of the cutting mechanism 18 morcellates the tissue 98 into morcellated tissue 100, as shown in FIG. 11. The smaller portions of the morcellated tissue 100 will then drop into the containment mechanism 12. The morcellating device 10 is then removed from the trocar 94 and the morcellated tissue 100 is aspirated out of the containment mechanism 12. The hollow shaft 38 is disconnected from the housing 36 and the remaining morcellated tissue 100 is recovered from the cutting mechanism 18.

Turning now to FIG. 18, in another embodiment, the deployment mechanism 76 can be used to deploy the containment mechanism 12 and cutting mechanism 18 combination into the external environment 62. To begin, the containment mechanism 12 and cutting mechanism 18 combination are positioned inside the deployment mechanism 76. A handle 77 of the deployment mechanism 76 is then pushed in until the containment mechanism 12 and cutting mechanism 18 are deployed in the external environment 62. Note that the deployment mechanism 76 includes a slit 78 for the drawstring-like closing mechanism 74 to come through and be released when the deployment mechanism 76 is removed from the trocar 94. Also, note that the bundles 34 are coupled to the movable member 40 of the morcellating device 10 prior to the containment mechanism 12 and cutting mechanism 18 combination being deployed into the external environment 62. Once deployed, the deployment mechanism 76 is removed from the trocar 94 and the morcellating device 10 is inserted into the trocar 94.

Similar to the previous embodiments, a tool, such as a tenaculum (not shown) can then be used to grasp the perimeter portion 32 of the containment mechanism 12 and position the perimeter portion 32 around the entire outer surface 56 of the end portion 50 of the hollow shaft 38. Prior to coupling the perimeter portion 32 of the containment mechanism 12 to the entire outer surface 56 of the hollow shaft 38, the tissue 98 is placed into the interior space 16 of the containment mechanism 12 through the opening 66. The closing mechanism 74 is then pulled by the user to seal the containment mechanism 12 around the outer surface 56 of the end portion 50. The remaining process of morcellating the tissue 98 is the same as the embodiments previously described.

After the tissue 98 is morcellated, a larger portion of the morcellated tissue 100 remains in the cutting mechanism 18 and the remaining portions of the morcellated tissue 100 remain in the containment mechanism 12, as shown in FIG. 11. The portions of the morcellated tissue 100 that remain in the cutting mechanism 18 inside the hollow shaft 38 need to be extracted for pathology. Therefore, the hollow shaft 38 can be openable, for example by a hinge, or, as previously stated, the hollow shaft 38 can be coupled with threads to the housing 36 so that the hollow shaft 38 can be screwed into the housing 36 and simply unscrewed from the housing 36 once the morcellating procedure is complete to gain access to the morcellated tissue 100. Alternatively, a hook (not shown) could be used to pull the cutting mechanism 18 out from the inner space 60 of the hollow shaft 38 such that the opening 66 of the cutting mechanism 18 is below the end portion 50 of the hollow shaft 38 and then the morcellated tissue 100 can be removed from the cutting mechanism 18.

The morcellated tissue 100 remaining in the containment mechanism 12 can be removed through aspiration, a pulling device 84 or through a tissue removal insertion tube (not shown) that is similar in size to the trocar 94, shown in FIG. 18. The tissue removal insertion tube can be made of a material strong enough to withstand the force of pulling the containment mechanism 12 through the insertion tube. The tissue removal insertion tube will have an outer diameter close to that of the trocar 94 and the insertion tube can have rounded edges and/or a chamfer to ensure that the containment mechanism 12 will not be cut by the edges of the insertion tube when it is forcibly pulled. Alternatively, the containment mechanism 12 can be pulled out of the body 79 by another motor-actuated device (not shown) which functions in a similar way to the morcellating device 10. The tissue removal insertion tube can be attached to a movable member and a motor, and the user can attach the drawstring-type closing mechanism to the movable member and actuate the motor, thereby pulling the containment mechanism 12 through the tissue removal insertion tube. The motor-actuated device could be reusable since it does not come into direct contact with morcellated tissue 100 and is easily disassembled and sterilized. Further, the motor-actuated device could have a maximum force limited to a point such that the containment mechanism 12 cannot break and the user could move to aspiration if the morcellated tissue 100 proved too difficult to pull out of the external environment 62, as shown in FIG. 18.

The morcellating device 10 can further include sensors and feedback mechanisms to assist the user during a laparoscopic procedure. As shown in FIGS. 11 and 18, a sensor 64 is disposed on the hollow shaft 38. The sensor 64 can be positioned on either the inner surface 58 or the outer surface 56 of the hollow shaft 38, and the sensor can be mechanical, electromechanical or optomechanical. An indicator 72 can be positioned in the trocar 94 and the indicator 72 is in electrical communication with the sensor 64. The sensor 64 can sense how far the hollow shaft 38 is inserted into the trocar 94 at a specific distance and provide feedback for the user, thereby preventing the hollow shaft 38 from being inserted too far into the trocar 94. The indicator 72 will automatically alert the user if the hollow shaft 38 is inserted past the specific distance. Alternatively, the hollow shaft 38 can have a mechanical block or marking 73 on the outer surface 56 that is visible to the user as the hollow shaft 38 is inserted into the trocar 94.

A load sensing mechanism can also be implemented to assist the user during a laparoscopic procedure. As shown in FIG. 10, a sensor 65 that senses load variations on the retractor mechanism 22 and is in electrical communication with the controller 48, as shown in FIG. 1. The controller 48 is in electrical communication with the motor 24 such that when the sensor 65 senses a specific load threshold, the controller 48 automatically stops the motion of the motor 24, thereby stopping the rotation of the retractor mechanism 22 and motion of the containment mechanism 12 and the cutting mechanism 18. Above the load threshold, the controller 48 can decrease the motion of the motor 24, thereby decreasing the rotation of the retractor mechanism 22 and the motion of the containment mechanism 12 and the cutting mechanism 18. Similarly, below the load threshold, the controller can increase the motion of the motor 24, thereby increasing the rotation of the retractor mechanism 22 and the motion of the containment mechanism 12 and the cutting mechanism 18.

Another feedback mechanism is best shown in FIGS. 11 and 18, where the sensor 64 is disposed on the hollow shaft 38. The sensor 64 is in electrical communication with the controller 48 and the controller 48 is in electrical communication with the motor 24. The sensor 64 can be positioned on either the inner surface 58 or the outer surface 56 of the hollow shaft 38, and the sensor can be mechanical, electromechanical, or optomechanical. The sensor senses when the cutting mechanism 18 is fully retracted into the hollow shaft 38 and when the tissue 98 is morcellated and sends a signal to the controller 48 which automatically stops motion of the motor 24. Automatically stopping the motion of the motor 24 stops the rotation of the retractor mechanism 22 so that the cutting mechanism 18 and morcellated tissue 100 do not get wound into the retractor mechanism 22 and potentially contaminate the housing 36 of the morcellating device 10. The above described feedback mechanism further prevents the morcellated tissue 100 from being caught in the retractor mechanism 22, making the morcellated tissue 100 unsuitable for pathology. Alternatively, an audible sound, such as a beeping noise, could be sounded to alert the user to release the actuator 46, thereby stopping motion of the motor 24.

Additionally, as shown in FIG. 7, a stopper 68 coupled to the bundles 34 of the cutting mechanism 18 can be used as a feedback mechanism. Once the bundles 34 are retracted to the position where the stopper 68 makes contact with the retractor mechanism 22, the user can feel a resistance indicating that the cutting mechanism 18 is in the fully retracted position 52. This feedback mechanism can inhibit the internal components of housing 36 from being contaminated from the morcellated tissue 100 and the morcellated tissue 100 from being crushed/caught in the bundles 34.

Figure 19:
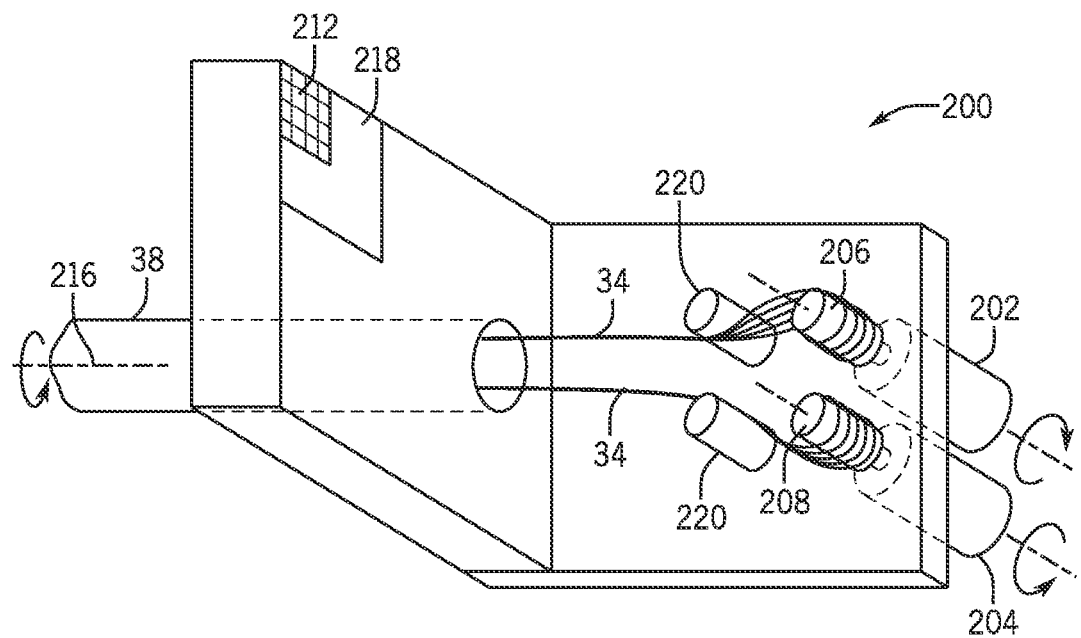
FIG. 19 is a top perspective view of a dynamic torque balancing mechanism for the morcellating device.
Figure 20:
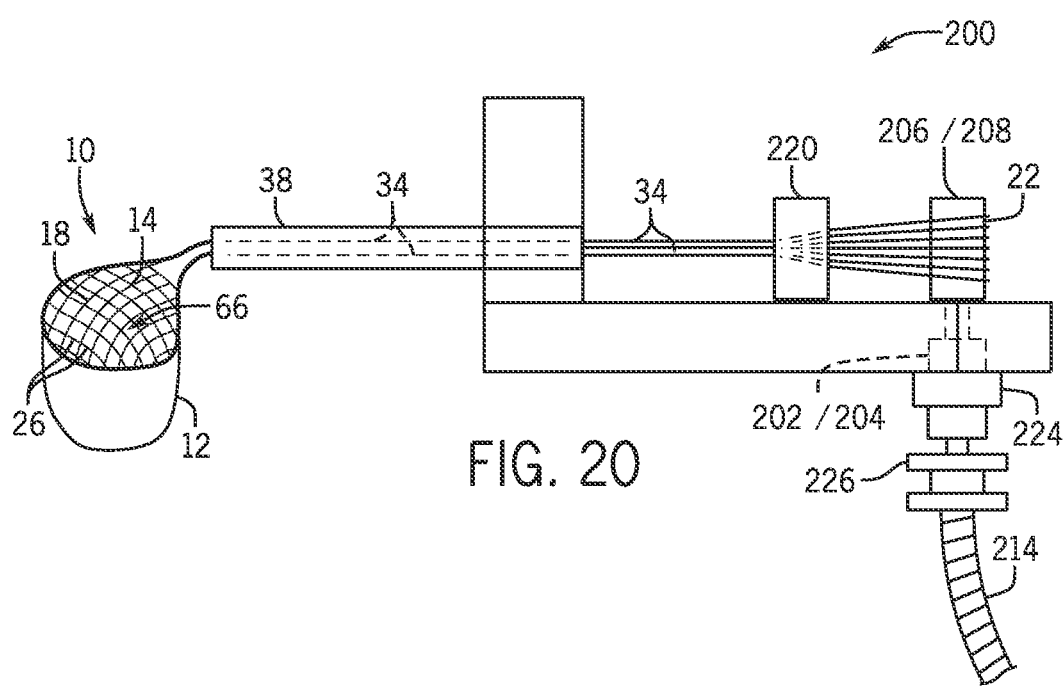
FIG. 20 is a side perspective view of the dynamic torque balancing mechanism for the morcellating device of FIG. 19.

Turning now to FIGS. 19 and 20, the morcellating device 10 can further include a dynamic torque balancing mechanism 200. The dynamic torque balancing mechanism 200 includes an accelerometer 212 (e.g., a piezoelectric accelerometer), a first secondary motor 202 attached to a first movable member 206, a second secondary motor 204 coupled to a second movable member 208, a set of free pegs 220 to guide the bundles 34, a coupling gear 224, a gear reduction mechanism 226, and a torque shaft 214 coupled to the main motor 24 of FIG. 1. The first and second secondary motors 202, 204 are substantially parallel and coupled to the accelerometer 212 and extend past the first and second movable members 206, 208, but are still disposed within the housing 36 of the morcellating device 10. The bundles 34 of the cutting mechanism 18 are evenly coupled to the first and second movable members 206, 208. When the force F, which is created by the retractor mechanism 22 retracting the cutting mechanism 18 into the hollow shaft 38 and cutting the tissue 98, as shown in FIG. 10, is above a certain threshold, the bundles 34 on the opposing side will be retracted in with more force by the corresponding secondary motor 202, 204 to center the center of mass of the tissue (not shown) over the inner space 60 of the hollow shaft 38, thereby providing a counter-balance. The RPM of the relevant secondary motor 202, 204 is automatically controlled by and adjusted based on the accelerometer 212 to change the RPM of the relevant motor(s) 202, 204 and balance torque.

Figure 21:
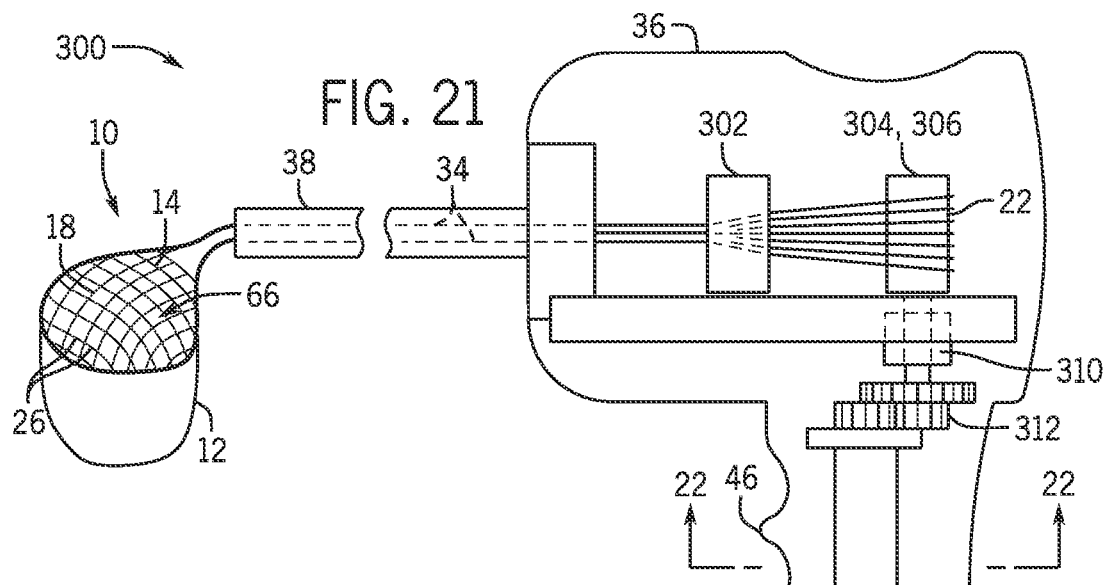
FIG. 21 is a side perspective view of a static torque balancing mechanism for the morcellating device.
Figure 22:
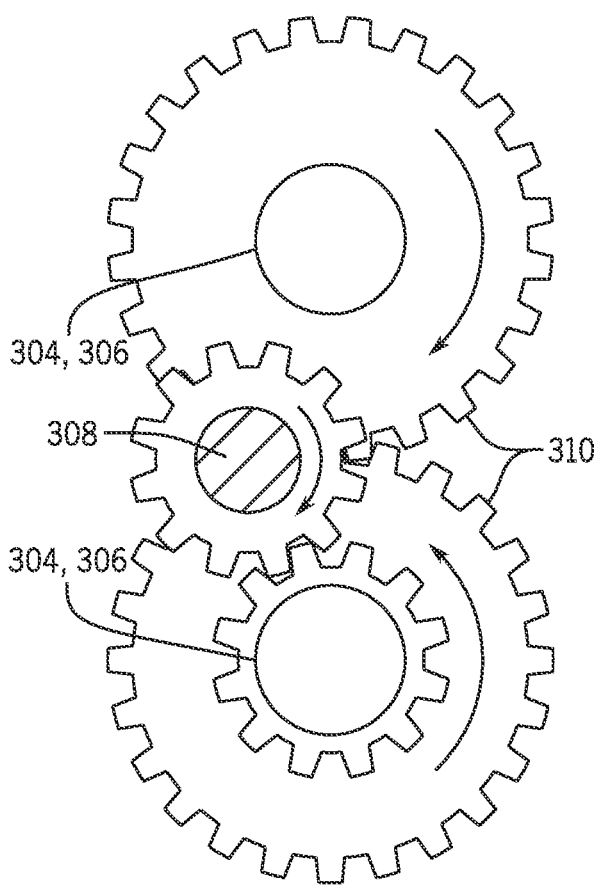
FIG. 22 is a perspective view of a set of coupling gears which activate the static torque balancing mechanism of the morcellating device of FIG. 21.

Alternatively, the morcellating device 10 can further include a static torque balancing mechanism 300 as shown in FIGS. 21 and 22. The static torque balancing mechanism 300 includes the main motor 24 aligned with the axis of rotation 216 of the hollow shaft 38 (shown in FIG. 21) or the axis of the handle 42 which is perpendicular to the axis of rotation 216 of the hollow shaft 38. The static torque balancing mechanism 300 further includes free pegs 302 to guide the bundles 34, coupling gears 310, a gear reduction 312 and a torque shaft 314. The motor 24 activates the torque shaft 314 which activates the retractor mechanism 22, thereby turning the first movable member 304 and the second movable member 306 simultaneously in opposite directions by using appropriate coupling gears 310. This potentially greatly reduces the overall torque of the first and second movable members 304, 306 as the retractor mechanism 22 retracts the cutting mechanism 18 into the hollow shaft 38.

The morcellating device 10 can further include a gas flow control element (not shown) for controlling the flow of gas through the hollow shaft 38 and the morcellating device 10. The morcellating device 10 is unusable without the gas flow control element since otherwise the gas extending the abdomen or external environment 62, shown in FIG. 18, escapes rapidly and prevents visualization. Thus, there should be a gas flow control element located in either the hollow shaft 38 or the body 79 that prevents rapid escape. For instance, the gas flow control element could be a mechanical valve that could be sealed off while gas re-accumulates in the body 79.

The present morcellating device 10 described above has several advantages over conventional morcellating devices. First, the present morcellating method could serve in place for any procedure that is done with morcellation, as well as expand the range of accessible procedures. For instance, organs, such as kidneys, which are hard to grab and remove from the patient's body 79 in one piece because the tissue is soft can be removed with the morcellating device 10 and method as described above. Further, a surgery which is currently not done laparoscopically, is a hysterectomy in the presence of ovarian cancer. Since cancerous tissue should not be morcellated with conventional techniques due to the risk of spreading cancer/seeding, the operation is done via laparotomy. The present morcellating device 10, however could be used during a hysterectomy while reducing the risk of seeding. The morcellating device 10 can further be implemented into other procedures such as nephrectomy (kidney removal), splenectomy (spleen removal) and cholecystectomy (gallbladder removal).

Additionally, the morcellating device 10 is intrinsically scalable across tumor sizes, thereby opening the possibility to make smaller-than-standard incisions for smaller pieces of tissue 98 that require removal and allowing even very large tissue to be removed without laparotomy. Further, the morcellating device 10 is economical because the cutting mechanism 18, constructed of the plurality of compliant elongate members 26, is bladeless. Conventional morcellating blades tend to be rather expensive. Also, having several reusable parts makes the morcellating device more economical.

The present morcellating device 10 can also potentially save on operating room time, while still being able to capture larger and more dense tissue 98 than current morcellators can reasonably handle. Current morcellators take time for grabbing/re-grabbing the tissue, time for coring, time for setup/re-setup when the blades break or the motor overheats, time for grabbing the morcellated tissue, and time for aspiration. However, the present morcellating device 10 and tissue retrieval method automatically cuts the whole piece of tissue 98 into the pre-specified sizes in one pass, and the speed is determined by the parameters of the motor (i.e., the rotation frequency), thereby potentially reducing time in the operating room.

An additional advantage of the morcellating device 10 is the potential for automation and use in robotic surgery. Robotic surgeries (where the robot is controlled by a human) are currently slow and expensive. Tissue 98 to be removed from the body 79 is targeted and the standard morcellation process is used with all of the pitfalls, including dropping morcellated tissue 100 into the body 79. The advantages of the morcellating device 10 previously mentioned would carry over to a robotic procedure. In potentially "automatic" robotic surgical procedures that may be developed, the conventional method would carry more disadvantages than direct human surgeons have since for example an automated robot would have to re-find the pieces of morcellated tissue 100 and waste computation time. The present morcellating device could lead to simpler processes for automatic robotic surgery (i.e., tracking/identification, placement of the tissue 98 into the containment mechanism 12) by eliminating the need for excess steps, potentially improving procedure time and minimizing "lost" pieces of the morcellated tissue 100.

What is claimed is:

1. A method of using a surgical device for isolating and dissecting a tissue mass into smaller pieces, comprising:
providing a surgical device including a container for isolating a tissue mass during a surgical procedure, said container defining an aperture and an interior space, said aperture being in fluid communication with said interior space, the device further including at least one elongate cutter having a first end and a second end, each said end being coupled to a motorized drive, at least a portion of said at least one elongate cutter being disposed within said container, said at least one elongate cutter being configured to at least partially surround said tissue mass prior to performing a cutting operation;
introducing at least a portion of the surgical device into a patient's body proximate the tissue mass;
introducing the tissue mass into the interior space of the surgical device such that the at least one elongate cutter at least partially surrounds said tissue mass; and
actuating the motorized drive to cause tension to be applied to said first end and said second end of said at least one elongate cutter to at least partially withdraw said at least one elongate cutter outwardly from said container through said aperture to cut through said tissue mass, wherein partially withdrawing said at least one elongate cutter includes independently and selectively applying tension to each of said first end and said second end of said at least one elongate cutter by way of the motorized drive.

2. The method 1, wherein when said motorized drive is configured to apply tension that exceeds a predetermined threshold value in order to advance either the first end or the second end of said at least one elongate cutter as detected by at least one load sensor, and further wherein tension applied by said motorized drive is adjusted by a controller to provide a counter balancing force that is configured to center a center of mass of the tissue mass with respect to a central longitudinal axis of the motorized surgical instrument.

3. The method of claim 1, wherein said at least one elongate cutter includes a plurality of parallel cutters that are joined at first and second ends.

4. The method of claim 3, wherein said plurality of parallel cutters form at least one bundle.

5. The method of claim 1, wherein each of said first end and said second end of said at least one elongate cutter is operably coupled to a separate motor to selectively applying tension to each of said first end and said second end of said at least one elongate cutter.

6. The method of claim 1, wherein the motorized drive of the surgical device is off-board of a housing portion of the surgical device that encloses a part of the retractor mechanism.

7. The method of claim 6, wherein the housing portion of the surgical device is coupled to a surgical robot.

8. The method of claim 1, further comprising applying a vibrational force to the at least one elongate cutter as it cuts through the tissue mass.

9. The method of claim 1, further comprising directing gas flow through the surgical device into the patient.

10. The method of claim 9, wherein directing gas flow through the surgical device is controlled by way of a flow control element.

11. The method of claim 1, wherein the surgical device is coupled to a surgical robot.

12. The method of claim 1, wherein the surgical procedure includes a hysterectomy, and the tissue mass includes at least a portion of the patient's uterus.

13. The method of claim 1, wherein the surgical procedure includes a nephrectomy, and the tissue mass includes at least a portion of one of the patient's kidneys.

14. The method of claim 1, wherein the surgical procedure includes a splenectomy, and the tissue mass includes at least a portion of the patient's spleen.

15. The method of claim 1, wherein the surgical procedure includes a cholecystectomy, and the tissue mass includes at least a portion of the patient's gall bladder.

\* \* \* \* \*